(12) United States Patent
Zlokarnik et al.

(10) Patent No.: US 6,284,461 B1
(45) Date of Patent: Sep. 4, 2001

(54) USE OF INHIBITORS IN REPORTER ASSAYS

(75) Inventors: Gregor Zlokarnik; Luxin Feng, both of San Diego, CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/067,612

(22) Filed: Apr. 28, 1998

(51) Int. Cl.⁷ .................. C12Q 1/68; C12Q 1/34
(52) U.S. Cl. ................................ 435/6; 435/18
(58) Field of Search .................. 435/18, 231, 4, 435/6, 29

(56) References Cited

U.S. PATENT DOCUMENTS

| | | | |
|---|---|---|---|
| 5,741,657 | 4/1998 | Tsien et al. | 435/18 |
| 5,861,269 * | 1/1999 | Visor et al. | 435/26 |
| 5,928,888 * | 7/1999 | Whitney | 435/29 |

FOREIGN PATENT DOCUMENTS

| | | |
|---|---|---|
| WO 96/30540 | 10/1996 | (WO) . |
| WO 98/13353 | 4/1998 | (WO) . |

OTHER PUBLICATIONS

DeBriune and Yde, Carbohydrate Research 56:153–164 (1977).
Molecular Probes Product Information Sheet, Fluorescein Digalactoside (1997).
Moore et al., Analytical Biochemistry 247:203–209 (1997).
Young et al., Analytical Biochemistry 215:24–30 (1993).
Zlokarnik et al., Science 279:84–88 (1998).
Fiering, et al Cytometry 12:291–301 (1991).

* cited by examiner

*Primary Examiner*—Elizabeth Slobodyansky
(74) *Attorney, Agent, or Firm*—Gray Cary Ware & Freidenrich LLP; Lisa A. Haile

(57) ABSTRACT

The present invention relates to methods for increasing the signal-to-noise ratio of an enzyme assay by contacting a sample comprising a membrane compartment with an inhibitor of an enzyme, contacting the sample with a substrate for the enzyme, and determining the activity of the enzyme. The method can be in a heterogeneous or homogeneous format. The methods of the present invention can be used for a variety of purposes, such as increasing the dynamic range of an enzyme assay, extending the useful loading time or assay measurement time of an enzyme assay, profiling the level of an enzyme in a sample, modulating the threshold activity of an enzyme assay, screening test compounds for activity, identifying modulators, identifying an inhibitor of an enzyme, and detecting membrane permeability. The present invention also relates to compounds useful in these methods.

14 Claims, 6 Drawing Sheets

Calvulanic acid  Imipenem  HOB – 1 – 70

USE OF INHIBITORS IN REPORTER ASSAYS

FIELD OF THE INVENTION

The present invention is directed to compositions that inhibit reporter enzyme activity within a cell during enzymatic assays. These compositions can be used in methods that detect the activity of the reporter enzyme.

INTRODUCTION

A reporter gene assay measures the activity of a gene's promoter. It takes advantage of molecular biology techniques, which allow one to put heterologous genes under the control of any promoter and introduce the construct into the genome of a mammalian cell (see, Gorman et al., Mol. Cell Biol. 2:1044–1051 (1982); Alam et al., Anal. Biochem. 188:245–254 (1990)). Activation of the promoter induces the expression of the reporter gene, as well as, or instead of, the endogenous gene. By design, the reporter gene codes for a reporter protein that can easily be detected and measured. Commonly, the reporter protein is a reporter enzyme activity that converts a commercially available substrate into a product. This conversion can be conveniently followed by direct optical measurement and may allow for the quantification of the amount of reporter enzyme activity produced.

Reporter genes are commercially available on a variety of plasmids for the study of gene regulation in a large variety of organisms (see, Alam et al., supra, 1990). Promoters of interest can be inserted into multiple cloning sites provided for this purpose in front of the reporter gene on a plasmid (see, Rosenthal, Methods Enzymol. 152:704–720 (1987); Shiau et al., Gene 67:295–299 (1988)). Standard techniques are used to introduce these reporter genes into a cell type or whole organism (such as described in Sambrook et al. Molecular cloning, Cold Spring Harbor Laboratory Press (1989)). Resistance markers provided on a plasmid can then be used to select for successfully transfected cells.

Ease of use and the large signal amplification make this technique increasingly popular in the study of gene regulation. Every step in the cascade of DNA→RNA→Enzyme→Product amplifies the next one in the sequence. Generally, the further down in the cascade one measures, the more signal one obtains.

In a preferred reporter gene assay, the reporter gene, associated with or without a promoter, is transfected into cells, either transiently or stably. Activation of the reporter gene by, for examiner, the activation of a receptor, leads to a change in reporter enzyme activity levels via transcriptional and translational events. The amount of reporter activity enzyme present can be measured via its enzymatic action on a substrate. The substrate can be a small uncharged molecule that, when added to the extracellular solution, can penetrate the plasma membrane to encounter the reporter enzyme activity. A charged molecule can also be employed, but the charges can be masked by groups that will be cleaved by endogenous cellular enzymes (e.g., esters cleaved by cytoplasmic esterases).

Substrates that exhibit changes in their fluorescence spectra upon interaction with a reporter enzyme activity are particularly desirable due to the sensitivity of assays that use such substrates. In some assays, the fluorogenic substrate is converted to a fluorescent product. Alternatively, the fluorescent substrate changes fluorescence properties upon conversion by the reporter enzyme activity. The product of such reporter enzyme activity should be very fluorescent to obtain maximal signal and very polar, to preferably stay inside the cell.

To achieve the high sensitivity in a reporter enzyme activity assay one has to maximize the amount of signal generated by a single reporter enzyme. An optimal reporter enzyme activity will convert $10^5$ substrate molecules per second under saturating conditions (see, Stryer, Introduction to enzymes. In: Biochemistry, New York, W. H. Freeman and Co. (1981), pp. 103 to 134). Beta-lactamases will cleave about $10^3$ molecules of their preferred substrates per second (Chang et al., Proc. Natl. Acad. Sci. USA 87:2823–2827 (1990)). Using a fluorogenic substrate one can obtain up to $10^6$ photons per fluorescent product produced, depending on the type of dye used, when exciting with light of the appropriate wavelength. The signal terminates with the bleaching of the fluorophore (Tsien et al., Handbook of Biological Confocal Microscopy, ed: Pawley, J. B. Plenum Publishing Co (1990), pp. 169–178). These numbers illustrate the theoretical magnitude of signal obtainable in this type of measurement. In practice, a minute fraction of the photons generated will be detected, but this holds true for fluorescence, bioluminescence or chemiluminescence. A good fluorogenic substrate for a reporter enzyme activity should have a high turnover at the enzyme in addition to good optical properties such as high extinction and high fluorescence.

However, reporter genes can be expressed at low background levels even when the assay is designed not to have the reporter gene expressed. Under these circumstances, low levels of background reporter enzyme activity exist. Background reporter enzyme activity can cause the signal-to-noise ratio of the assay to suffer because de novo reporter enzyme activity (signal) is affected by background reporter enzyme activity (noise). The present invention solves these problems, and provides related benefits as well.

SUMMARY OF THE INVENTION

One aspect of the present invention is a method for increasing the signal-to-noise ratio of a reporter enzyme activity assay by contacting a sample comprising a membrane compartment containing a reporter enzyme activity with an inhibitor of the reporter enzyme activity, contacting the sample with a substrate for the reporter enzyme activity, and determining the activity of the reporter enzyme activity. Preferably, the inhibitor of the reporter enzyme activity is an irreversible inhibitor of the reporter enzyme and is membrane permeant. This method is particularly useful in intracellular assays where the inhibitor of the reporter enzyme activity is used to reduce background reporter enzyme activity.

Another aspect of the present invention is a homogeneous method for increasing the signal-to-noise ratio of a reporter enzyme activity assay by contacting a sample comprising a membrane compartment containing a reporter enzyme activity with an inhibitor of the reporter enzyme activity, contacting the sample with a substrate for the reporter enzyme activity, contacting the sample with a composition that degrades the inhibitor of the reporter enzyme activity, and determining the activity of the reporter enzyme activity.

A further aspect of the present invention is a method for increasing the dynamic range of a reporter enzyme activity assay by contacting a sample comprising a membrane compartment containing a reporter enzyme activity with an inhibitor of a reporter enzyme activity, contacting the sample with a substrate for the reporter enzyme activity, and determining reporter enzyme activity. This method is particularly useful for increasing the detection range of a reporter enzyme activity assay that has high background reporter enzyme activity and low substrate concentration.

Another aspect of the present invention is a method for extending the useful loading time or assay measurement time of a reporter enzyme activity assay by contacting a sample comprising a membrane compartment containing a reporter enzyme activity with an inhibitor of a reporter enzyme activity, contacting the sample with a substrate for the reporter enzyme activity, and determining reporter enzyme activity. This method is particularly useful for increasing the detection range of an assay that has high background reporter enzyme activity and low substrate concentration.

A further aspect of the present invention is a method for profiling the level of a reporter enzyme activity by contacting a sample comprising a membrane compartment containing a reporter enzyme activity with an inhibitor of a reporter enzyme activity, contacting the sample with a substrate for the reporter enzyme activity, and determining reporter enzyme activity.

Another aspect of the present invention is a method for detecting the activity of a reporter enzyme activity by contacting a sample comprising a membrane compartment containing a reporter enzyme activity with an inhibitor of a first reporter enzyme activity (wherein said inhibitor of a first reporter enzyme activity does not inhibit a second reporter enzyme activity), contacting the sample with a substrate for the first reporter enzyme activity and a substrate for the second reporter enzyme activity (wherein the substrate for the first reporter enzyme activity and the substrate for the second reporter enzyme activity are the same), and determining the first reporter enzyme activity, the second reporter enzyme activity, or both. This method is particularly useful for assays having multiple reporter enzyme activities.

A further aspect of the present invention is a method for modulating the threshold activity of a reporter enzyme activity assay by contacting a sample comprising a membrane compartment containing a reporter enzyme activity with an inhibitor of a reporter enzyme activity, contacting the sample with a substrate for the reporter enzyme activity, and determining the reporter enzyme activity. This method is particularly useful for detecting a threshold activity of a reporter enzyme activity.

Another aspect of the present invention is a method for screening test chemical for activity by contacting a sample comprising a membrane compartment containing a reporter enzyme activity with an inhibitor of a reporter enzyme activity, contacting the sample with at least one test chemical, contacting the sample with a substrate for the reporter enzyme activity, and determining the reporter enzyme activity. This method is particularly useful for identifying test chemicals having a therapeutic activity in a reporter enzyme activity assay.

A further aspect of the present invention is a method for identifying a modulator by contacting a sample comprising a membrane compartment containing a reporter enzyme activity with an inhibitor of a reporter enzyme activity, contacting the sample with at least one test chemical, contacting the sample with a substrate for the reporter enzyme activity, and determining the reporter enzyme activity. This method is particularly useful for identifying compounds having a therapeutic activity in a reporter enzyme activity assay.

Another aspect of the present invention is a method for identifying a modulator, such as an inhibitor, of a reporter enzyme activity by contacting a sample comprising a membrane compartment with at least one test chemical, contacting the sample with a substrate for the reporter enzyme activity, and determining the reporter enzyme activity, wherein the reporter enzyme activity is within said membrane compartment.

A further aspect of the present invention is a method for detecting membrane permeability by contacting a sample comprising a membrane compartment containing a reporter enzyme activity with a non-membrane-permeant inhibitor of the reporter enzyme activity, contacting the sample with a substrate for the reporter enzyme activity, and determining the reporter enzyme activity. This method is particularly useful for detecting membrane permeability in response to various stimuli, such as test chemicals.

Another aspect of the present invention is a composition comprising a membrane compartment, said membrane compartment comprising a reporter enzyme activity, and an inhibitor of the reporter enzyme activity. These compositions are particularly useful in the methods of the present invention and can be provided in kits to practice at least one method of the present invention.

DETAILED DESCRIPTION

Definitions

Figure 1:
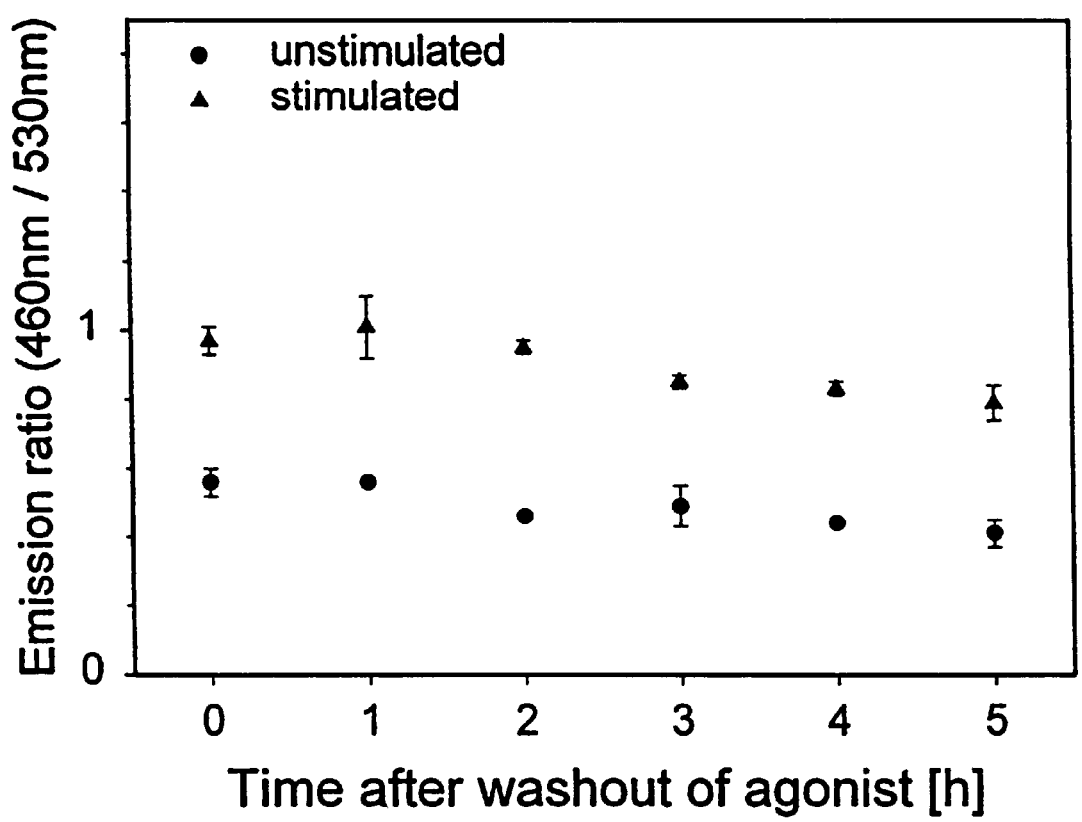
FIG. 1 represents the effects of removal of a stimulus from cells that expressed cytosolic beta-lactamase reporter enzyme activity in response to that stimulus.

Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described below, are those well known and commonly employed in the art. Standard techniques are used for recombinant nucleic acid methods, polynucleotide synthesis, and microbial culture and transformation (e.g., electroporation, and lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The nomenclature used herein, and the laboratory procedures in analytical chemistry, organic synthetic chemistry, and pharmaceutical formulation described below, are those well known and commonly employed in the art. Standard techniques are used for chemical syntheses, chemical analyses, pharmaceutical formulation and delivery, and treatment of patients. As employed throughout the disclosure, the following terms, unless otherwise indicated, shall be understood to have the following meanings:

"Fluorescent donor moiety" refers to a fluorogenic compound or part of a compound (including a radical) which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

"Quencher" refers to a chromophoric molecule or part of a compound that is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and excitation coupling such as the formation of dark complexes.

"Acceptor" refers to a quencher that operates via fluorescence resonance energy transfer. Many acceptors can re-emit the transferred energy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, and di- and tri-phenylmethanes.

"Dye" refers to a molecule or part of a compound that absorbs specific frequencies of light, including but not limited to ultraviolet light. The terms "dye" and "chromophore" are synonymous.

"Fluorophore" refers to a chromophore that fluoresces.

"Membrane-permeant derivative" refers a chemical derivative of a compound that increases membrane permeability of the compound. These derivatives are made better able to cross cell membranes, i.e. membrane permeant, because hydrophilic groups are masked to provide more hydrophobic derivatives. Also, the masking groups are designed to be cleaved from the fluorogenic substrate within the cell to generate the derived substrate intracellularly. Because the substrate is more hydrophilic than the membrane permeant derivative it becomes preferentially localized within a membrane compartment, such as a cell.

"Isolated polynucleotide" refers to a polynucleotide of genomic, cDNA, or synthetic origin or some combination there of, which by virtue of its origin, the "isolated polynucleotide" (1) is not associated with the cell in which the "isolated polynucleotide" is found in nature, or (2) is operably linked to a polynucleotide which it is not linked to in nature.

"Isolated protein" refers to a protein of cDNA, recombinant RNA, or synthetic origin, or some combination thereof, which by virtue of its origin the "isolated protein" (1) is not associated with proteins found as it is normally found with in nature, or (2) is isolated from the cell in which it normally occurs, or (3) is isolated free of other proteins from the same cellular source, e.g. free of human proteins, or (4) is expressed by a cell from a different species, or (5) does not occur in nature.

"Polypeptide" as used herein as a generic term to refer to native protein, fragments, or analogs of a polypeptide sequence. Hence, native protein, fragments, and analogs are species of the polypeptide genus. Preferred beta-lactamase polypeptides include those with the polypeptide sequences set forth in WO 96/30540, to Tsien et al., published Oct. 3, 1996, any other polypeptide or protein having similar beta-lactamase activity as measured by one or more of the assays described herein. Beta-lactamase polypeptide or proteins can include any protein having sufficient activity for detection in the assays described herein. Such preferred beta-lactamase polypeptides are preferred reporter enzyme activities of the present invention.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to finction in their intended manner. A control sequence "operably linked" to a coding sequence is ligated in such a way that expression of the coding sequence is achieved under conditions compatible with the control sequences.

"Expression control sequence" refers to polynucleotide sequences that are necessary to effect the expression of coding and non-coding sequences to which they are ligated. The nature of such control sequences differs depending upon the host organism, in eukaryotes, such control sequences generally include promoter, ribosomal binding site, and transcription termination sequence; in prokaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences. Expression control sequences can include, for example, promoters, enhancers and repressors.

"Polynucleotide" refers to a polymeric form of nucleotides of at least ten bases in length, either ribonucleotides or deoxynucleotides or a modified form of either type of nucleotide. The term includes single and double stranded forms of DNA. "Genomic polynucleotide" refers to a portion of a genome. "Active genomic polynucleotide" or "active portion of a genome" refer to regions of a genome that can be up regulated, down-regulated or both, either directly or indirectly, by a biological process. "Directly," in the context of a biological process or processes, refers to direct causation of a process that does not require intermediate steps, usually caused by one molecule contacting or binding to another molecule (the same type or different type of molecule). For example, molecule A contacts molecule B, which causes molecule B to exert effect X that is part of a biological process. "Indirectly," in the context of a biological process or processes, refers to indirect causation that requires intermediate steps, usually caused by two or more direct steps. For example, molecule A contacts molecule B to exert effect X which in turn causes effect Y.

"Beta-lactamase polynucleotide" refers to a polynucleotide encoding a protein with beta-lactamase activity. Preferably, the protein with beta-lactamase activity can be measured in a FACS at about 22° using a CCF2/AM beta-lactamase substrate at a level of about 1,000 such protein molecules or less per cell. More preferably, the protein with beta-lactamase activity can measured be in a FACS at about 22° using a CCF2/AM beta-lactamase substrate at a level of about 300 to 1,000 such protein molecules per cell. More preferably, the protein with beta-lactamase activity can measured be in a FACS at about 22° using a CCF2/AM beta-lactamase substrate at a level of about 25 to 300 such protein molecules per cell. Proteins with beta-lactamase activity that require more than 1,000 molecules of such protein per cell for detection with a FACS at about 22° degrees using a CCF2/AM beta-lactamase substrate can be used and preferably have at least about 5% of the activity of the protein having the amino acid sequence of *E. coli* TREM in which the signal sequence has been replaced by ATG TGA (Kadonaga et al., J. Biol. Chem. 259:2149 (1984); WO 96/30540 to Tsien et al., Oct. 3, 1996). Preferred beta-lactamase substrates are described in WO 96/30540 to Tsien et al., published Oct. 3, 1996.

"Reporter gene" means a gene that encodes a reporter enzyme, such as they are known in the art or are later developed, such as a reporter enzyme activity. "Reporter enzyme" means an enzyme that encode a reporter enzyme that has a detectable read-out, such as beta-lactamase, beta-galactosidase, or luciferase (for beta-lactamase, see WO 96/30540 to Tsien, published Oct. 3, 1996). Preferably, reporter enzymes localize in the cytosol of a cell, such as cytosolic beta-lactamase. Reporter enzymes can be detected using methods known in the art, such as the use of chromogenic or fluorogenic substrates for reporter enzymes as such substrates are known in the art. Such substrates are preferably membrane permeant. Chromogenic or fluorogenic readouts can be detected using, for example, optical methods such as absorbance or fluorescence. A reporter gene can be part of a reporter gene construct, such as a plasmid or viral vector, such as a retrovirus or adeno-associated virus. A reporter gene can also be extra-chromosomal or be integrated into the genome of a host cell. The expression of the reporter gene can be under the control of exogenous expression control sequences or expression control sequences within the genome of the host cell. Under the latter configuration, the reporter gene is preferably integrated into the genome of the host cell.

"Reporter enzyme activity" refers to the activity of a reporter enzyme in a membrane compartment and includes background reporter enzyme activity and de novo reporter enzyme activity. "Background reporter enzyme activity" refers to a reporter enzyme activity that exists in a membrane compartment that was not made in response to a stimulus, such as a test chemical. "De novo reporter enzyme activity" refers to a reporter enzyme activity that appears in a membrane compartment in response to a stimulus. De novo reporter enzyme activity is a reporter activity that is generated due to the synthesis of new reporter enzyme activity, or due to transcriptional events, such as differential splicing of RNA encoding a reporter enzyme activity leading to expression of reporter enzyme activity in response to a stimulus. Other sources of de novo reporter enzyme activity include, but are not limited to, co-translational modifications of reporter enzyme activity, post-translational modifications of reporter enzyme activity, change in location of reporter enzyme activity, conformational change of reporter enzyme activity, and other mechanisms that lead to appearance of a reporter enzyme activity in response to a stimulus. Post-translational modifications that may lead to de novo reporter enzyme activity include, but are not limited to, phosphorylation, dephosphorylation, oligosaccharide attachment or removal, signal peptide cleavage, pre-protein or pro-protein processing, myristylation, or farnesylation of the reporter enzyme activity. A background reporter enzyme activity and a de novo reporter enzyme activity can be the same enzyme activity, such as beta-lactamase activity. In such instances, background reporter enzyme activity can be referred to as "noise" and de novo reporter enzyme.

"Reporter beta-lactamase" refers to a beta-lactamase that is inhibited by a beta-lactamase inhibitor, whereas an "inhibitor resistant beta-lactamase" refers to a beta-lactamase whose activity is inhibited less by a given beta-lactamase inhibitor than a reporter beta-lactamase. In such instances, the activity of the reporter beta-lactamase will be inhibited at a greater rate by a beta-lactamase inhibitor than will the activity of an inhibitor resistant beta-lactamase. Preferably, the inhibitor resistant beta-lactamase can degrade a beta-lactamase inhibitor in such a way that the reporter beta-lactamase activity is not inhibited by the beta-lactamase inhibitor. Preferably, such beta-lactamase inhibitors bind to the catalytic site of both the reporter beta-lactamase and the inhibitor resistant beta-lactarnase. Most preferably, the beta-lactamase activity is an irreversible inhibitor of the reporter beta-lactamase. Preferred reporter beta-lactamases have sequences such as set forth in WO 96/30540 to Tsien et al., issued Apr. 21, 1998.

"Sequence homology" refers to the proportion of base matches between two nucleic acid sequences or the proportion amino acid matches between two amino acid sequences. When sequence homology is expressed as a percentage, e.g., 50%, the percentage denotes the proportion of matches over the length of sequence from a desired sequence (e.g. beta-lactamase sequences, such as *E. coli* TREM wherein the signal sequence is replaced by ATG TGA (Kadonaga et al., J. Biol. Chem. 259:2149 (1984); WO 96/30540 to Tsien et al., published Oct. 3, 1996) that is compared to some other sequence. Gaps (in either of the two sequences) are permitted to maximize matching; gap lengths of fifteen bases or less are usually used, six bases or less are preferred with two bases or less more preferred. When using oligonucleotides as probes or treatments the sequence homology between the target nucleic acid and the oligonucleotide sequence is generally not less than seventeen target base matches out of twenty possible oligonucleotide base pair matches (85%); preferably not less than nine matches out of ten possible base pair matches (90%), and most preferably not less than 19 matches out of 20 possible base pair matches (95%).

"Selectively hybridize" refers to detectably and specifically bind. Polynucleotides, oligonucleotides and fragments thereof selectively hybridize to target nucleic acid strands, under hybridization and wash conditions that minimize appreciable amounts of detectable binding to nonspecific nucleic acids. High stringency conditions can be used to achieve selective hybridization as is known in the art and discussed herein. Generally, the nucleic acid sequence homology between the polynucleotides, oligonucleotides, and fragments thereof and a nucleic acid sequence of interest will be at least 30%, and, more typically, with preferably increasing homologies of at least about 40%, 50%, 60%, 70%, and 90%.

Typically, hybridization and washing conditions are performed at high stringency according to conventional hybridization procedures. Positive clones are isolated and sequenced. For illustration and not for limitation, a full-length polynucleotide corresponding to the nucleic acid sequence encoding beta-lactamases as set forth in WO 96/30540 to Tsien et al., published Oct. 3, 1996, may be labeled and used as a hybridization probe to isolate genomic clones from a the appropriate target library in λEMBL4 or λGEM11 (Promega Corporation, Madison, Wis.); typical hybridization conditions for screening plaque lifts (Benton and Davis (1978) Science 196: 180) can be: 50% formamide, 5×SSC or SSPE, 1 to 5×Denhardt's solution, 0.1 to 1% SDS, 100–200 µg sheared heterologous DNA or tRNA, 0–10% dextran sulfate, $1 \times 10^5$ to $1 \times 10^7$ cpm/ml of denatured probe with a specific activity of about $1 \times 10^8$ cpm/µg, and incubation at about 42° C. for about 6 to 36 hours. Prehybridization conditions are essentially identical except that probe is not included and incubation time is typically reduced. Washing conditions are typically 1 to 3×SSC, 0.1 to 1% SDS, 50 to 70° C. with change of wash solution at about 5 to 30 minutes. Cognate sequences, including allelic sequences, can be obtained in this manner.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching, gap lengths of five or less are preferred with two or less being more preferred. Alternatively, and preferably, two protein sequences (or polypeptide sequences derived from them of at least 30 amino acids in length) are homologous, as this term is used herein, if they have an alignment score of at more than five (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences, or parts thereof, are more preferably homologous if their amino acids are greater than or equal to 30% identity when optimally aligned using the ALIGN program.

"Corresponds to" refers to a polynucleotide sequence is homologous (i.e., is identical, not strictly evolutionarily related) to all or a portion of a reference polynucleotide sequence, or that a polypeptide sequence is identical to all or a portion of a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing such as the sequences encoding beta-lactamase set forth in WO 96/30540 to Tsien et al., published Oct. 3, 1996, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

"Polypeptide fragment" refers to a polypeptide that has an amino-terminal and/or carboxy-terminal deletion, but where the remaining amino acid sequence is usually identical to the corresponding positions in the naturally-occurring sequence deduced, for example, from a full-length cDNA sequence (e.g., the sequences encoding beta-lactamase set forth in WO 96/30540 to Tsien et al., published Oct. 3, 1996). "Beta-lactamase polypeptides fragment" refers to a polypeptide that is comprised of a segment of at least 25 amino acids that has substantial identity to a portion of the deduced amino acid sequence set forth in WO 96/30540 to Tsien et al., published Oct. 3, 1996, and which has at least one of the following properties: (1) specific binding to a beta-lactamase substrate, preferably cephalosporin, under suitable binding conditions, or (2) the ability to effectuate enzymatic activity, preferably cephalosporin backbone cleavage activity, when expressed in a mammalian cell. Typically, analog polypeptides comprise a conservative amino acid substitution (or addition or deletion) with respect to the naturally occurring sequence. Analogs typically are at least 300 amino acids long, preferably at least 500 amino acids long or longer, most usually being as long as full-length naturally-occurring polypeptide.

"Modulation" refers to the capacity to either enhance or inhibit a functional property of a biological activity or process (e.g., enzyme activity or receptor binding). Such enhancement or inhibition may be contingent on the occurrence of a specific event, such as activation of a signal transduction pathway, and/or may be manifest only in particular cell types.

The term "modulator" refers to a chemical (naturally occurring or non-naturally occurring), such as a biological macromolecule (e.g. nucleic acid, protein, non-peptide, or organic molecule), or an extract made from biological materials such as bacteria, plants, fungi, or animal (particularly mammalian) cells or tissues. Modulators are typically evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in assays described herein. The activity of a modulator may be known, unknown or partial known.

The term "test chemical" refers to a chemical to be tested by one or more method(s) of the invention as a putative modulator. A test chemical is usually not known to bind to the target of interest. The term "control test chemical" refers to a chemical known to bind to the target (e.g., a known agonist, antagonist, partial agonist or inverse agonist). The term "test chemical" does not typically include a chemical added as a control condition that alters the function of the target to determine signal specificity in an assay. Such control chemicals or conditions include chemicals that 1) non-specifically or substantially disrupt protein structure (e.g., denaturing agents (e.g., urea or guandium), chaotropic agents, sulfhydryl reagents (e.g., dithiotritol and beta-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). The term "test chemical" also does not typically include chemicals known to be unsuitable for a therapeutic use for a particular indication due to toxicity of the subject. Usually, various predetermined concentrations test chemicals are used for screening such as 0.01 microM, 0.1 microM, 1.0 microM, and 10.0 microM.

The term "target" refers to a biochemical entity involved a biological process. Targets are typically proteins that play a useful role in the physiology or biology of an organism. A therapeutic chemical binds to target to alter or modulate its function. As used herein, targets can include cell surface receptors, G-proteins, kinases, ion channels, phopholipases and other proteins mentioned herein.

The terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels (e.g. for polypeptides or polynucleotides) include, but are not limited to, the following: radioisotopes (e.g., $^{3}H$, $^{14}C$, $^{35}S$, $^{125}I$, 131I), fluorescent labels (e.g., FITC, rhodamine, and lanthanide phosphors), enzymatic labels (or reporter genes) (e.g., enzymatic reporter genes horseradish peroxidase, beta-galactosidase, luciferase and alkaline phosphatase; and non-enzymatic reporter genes (e.g., fluorescent proteins)), chemiluminescent, biotinyl groups, predetermined polypeptide epitopes recognized by a secondary reporter (e.g., leucine zipper pair sequences, binding sites for secondary antibodies, metal binding domains, and epitope tags). "Substantially pure" refers to an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

"Pharmaceutical agent or drug" refers to a chemical or composition capable of inducing a desired therapeutic effect when properly administered (e.g. using the proper amount and delivery modality) to a patient.

"Fluorescent moiety" refers to a moiety that exhibits fluorescence, as that term is known in the art. The fluorescent moiety can be of any chemical composition, such as protein or chemical, or a combination of the two. Preferably, the fluorescent moiety is a fluorescent chemical that is membrane permeant, such as a fluorescein, coumarin, rhodamine, nbd, or other such chemicals as they are known in the art (Molecular Probes Catalogue (1997); U.S. Pat. No. 5,631,169 to Lakowicz et al., issued May 20, 1997; U.S. Pat. No. 5,744,657 to Tsien et al., issued Apr. 21, 1998; and WO 96/30540 to Tsien et al., published Oct. 3, 1996).

"Membrane permeant" means that a compound can pass through a membrane, such as a cell membrane, such as a eukaryotic cell membrane, preferably a mammalian cell membrane. Preferably, membrane permeant compounds pass through a membrane without the assistance of transport molecules within a membrane, such as porins, but the present inventors recognizes such transport molecules as a mechanism of membrane permeability of compounds. Substantially membrane permeant means that a compound can pass through a membrane and accumulate within a cell to a concentration useful in the methods of the present invention. Preferably, membrane permeant compounds are at least as membrane permeant as CCF2/AM (see, U.S. Pat. No. 5,744,657 to Tsien et al., issued Apr. 21, 1998; and WO 96/30540 to Tsien et al., published Oct. 3, 1996). Furthermore, membrane permeant compounds are preferably more hydrophobic than membrane impermeant compounds, but no so hydrophobic so as to preferentially localize in a hydrophobic phase or in a membrane, such as a membrane of a mammalian cell.

"Membrane impermeant" means that a compound does not substantially pass through a membrane and is less membrane permeant than a membrane permeant compound, such as CCF2/AM. Membrane impermeant compounds are generally charged and preferably partition into an aqueous phase rather than into a hydrophobic phase.

"Fusion protein" means a chimeric protein as that term is known in the art. Fusion proteins can be made from nucleic acids encoding the fusion protein that are constructed using methods known in the art. A fusion protein preferably comprises a protein of interest and a specific binding member. The protein of interest can be any protein, but preferably has defined characteristics, such as location within a cell. For example, a protein of interest can be membrane bound, such as G-protein coupled receptors (GPCRs), cytoplasm, or associated with intracellular structures, such as the ER, Golgi, and the like.

"Inhibitor of an enzyme activity" means any type of inhibitor of an enzyme activity, such as competitive, non-competitive, irreversible, reversible, or allosteric inhibitors of an enzyme activity as such terms are known in the art. The enzyme activity can be a reporter enzyme activity or a background reporter enzyme activity the enzyme activity can inhibit the activity of either or both of a reporter enzyme activity and a background reporter enzyme activity. An "inhibitor of a reporter enzyme activity" in an inhibitor that inhibits a reporter enzyme activity, and an "inhibitor of a background reporter enzyme activity" is an inhibitor that inhibits a background reporter enzyme activity.

"Functionally irreversible inhibitor" or "substantially irreversible inhibitor" means that the rate of recovery of reporter enzyme activity is lower than the turnover time of the reporter enzyme activity that is inhibited. Preferably, the functionally irreversible inhibitor or substantially irreversible inhibitor has a disassociation rate from the enzyme that is at least ten times slower than the rate limiting step for catalysis of such enzyme, more preferably at least 100 times slower, and most preferably 1,000 times slower.

"Membrane compartment" means an aqueous compartment surrounded by a membrane. Membrane compartments can be cells, cell ghosts (such as a red blood cell ghost) or liposomes or other vesicle, including fragments of cells, such as, for example, microsomal preparations. A membrane can be part of a living cell, such as a plasma membrane or outer membrane of a prokaryotic cell or the plasma membrane or other membrane of a eukaryotic cell, or can be part of an enveloped virus.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Introduction

The present invention recognizes that inhibitors of a reporter enzyme activity in a membrane-compartment-based assay can be used to reduce background reporter enzyme activity. By reducing background reporter enzyme activity, the sensitivity of the assay can increase as a result of increased signal-to-noise ratios of such assays.

As a non-limiting introduction to the breadth of the invention, the invention includes several general and useful aspects, including:

1. A method for increasing the signal-to-noise ratio of a reporter enzyme activity assay by contacting a sample comprising a membrane compartment containing a reporter enzyme activity with an inhibitor of the reporter enzyme activity, contacting the sample with a substrate for the reporter enzyme activity, and determining the activity of the reporter enzyme activity, 2. A homogeneous method for increasing the signal-to-noise ratio of a reporter enzyme activity assay by contacting a sample comprising a membrane compartment containing a reporter enzyme activity with an inhibitor of the reporter enzyme activity, contacting the sample with a substrate for the reporter enzyme activity, contacting the sample with a composition that degrades the inhibitor of the reporter enzyme activity, and determining the activity of the reporter enzyme activity, 3. A method for increasing the dynamic range of a reporter enzyme activity assay by contacting a sample comprising a membrane compartment containing a reporter enzyme activity with an inhibitor of a reporter enzyme activity, contacting the sample with a substrate for the reporter enzyme activity, and determining reporter enzyme activity, 4. A method for extending the useful loading time or assay measurement time of a reporter enzyme activity assay by contacting a sample comprising a membrane compartment containing a reporter enzyme activity with an inhibitor of a reporter enzyme activity, contacting the sample with a substrate for the reporter enzyme activity, and determining reporter enzyme activity, 5. A method for profiling the level of a reporter enzyme activity by contacting a sample comprising a membrane compartment containing a reporter enzyme activity with an inhibitor of a reporter enzyme activity, contacting the sample with a substrate for the reporter enzyme activity, and determining reporter enzyme activity, 6. A method for detecting the activity of a reporter enzyme activity by contacting a sample comprising a membrane compartment containing a reporter enzyme activity with an inhibitor of a first reporter enzyme activity (wherein said inhibitor of a first reporter enzyme activity does not inhibit a second reporter enzyme activity), contacting the sample with a substrate for the first reporter enzyme activity and a substrate for the second reporter enzyme activity (wherein the substrate for the first reporter enzyme activity and the substrate for the second reporter enzyme activity are the same), and determining the first reporter enzyme activity, the second reporter enzyme activity, or both, 7. A method for modulating the threshold activity of a reporter enzyme activity assay by contacting a sample comprising a membrane compartment containing a reporter enzyme activity with an inhibitor of a reporter enzyme activity, contacting the sample with a substrate for the reporter enzyme activity, and determining the reporter enzyme activity, 8. A method for screening test chemical for activity by contacting a sample comprising a membrane compartment containing a reporter enzyme activity with an inhibitor of a reporter enzyme activity, contacting the sample with at least one test chemical, contacting the sample with a substrate for the reporter enzyme activity, and determining the reporter enzyme activity, 9. A method for identifying a modulator by contacting a sample comprising a membrane compartment containing a reporter enzyme activity with an inhibitor of a reporter enzyme activity, contacting the sample with at least one test chemical, contacting the sample with a substrate for the reporter enzyme activity, and determining the reporter enzyme activity, 10. A method for identifying a modulator, such as an inhibitor, of a reporter enzyme activity by contacting a sample comprising a membrane compartment with at least one test chemical, contacting the sample with a substrate for the reporter enzyme activity, and determining the reporter enzyme activity, wherein the reporter enzyme activity is within said membrane compartment, 11. A further aspect of the present invention is a method for detecting membrane permeability by contacting a sample comprising a membrane compartment containing a reporter enzyme activity with a non-membrane-permeant inhibitor of the reporter enzyme activity, contacting the sample with a substrate for the reporter enzyme activity, and determining the reporter enzyme activity, and 12. A composition comprising a membrane compartment said membrane compartment comprising a reporter enzyme activity, and an inhibitor of the reporter enzyme activity.

These aspects of the invention, as well as others described herein, can be achieved using the methods and compositions of matter described herein.

A first aspect of the present invention is a method for increasing the signal-to-noise ratio of a reporter enzyme activity assay, comprising the steps of contacting a sample comprising a membrane compartment containing a reporter enzyme activity with an inhibitor of a reporter enzyme activity, contacting said sample with a substrate for said reporter enzyme activity, and determining the activity of the reporter enzyme activity. In this aspect of the invention, the signal-to-noise ratio of the reporter enzyme activity assay is increased by decreasing background reporter enzyme activity using an inhibitor of the reporter enzyme activity.

Although not wishing to be bound to any mechanism, one possible mechanism for the present invention is that the membrane compartment contains background reporter enzyme activity. The background reporter enzyme activity is inhibited by a membrane permeant inhibitor of the reporter enzyme activity. The method is devised such that de novo reporter enzyme activity is uninhibited, or inhibited to a degree less than the background reporter enzyme activity, by the inhibitor (such as is washing the membrane compartments. When a substrate for the reporter enzyme activity is added to the sample, the signal (de novo reporter enzyme activity) to noise (background reporter enzyme activity) ratio is increased. Preferably, de novo reporter enzyme activity is made in response to a stimulus, such as a test chemical.

The sample can be any sample that contains a membrane compartment. For example, the sample can be a biological sample that includes a membrane compartment, such as an organism, such as a transgenic organism, or a sample derived from an organism, such as tissue, fluid containing cells, or cells. Cells can be in culture, such as a primary or continuous cell line. The membrane compartment can be a eukaryotic cell, such as a mammalian cell, or a human cell, or the membrane compartment can be a prokaryotic cell such as a bacterium. The sample can comprise a population of cells, such as a mixed population of cells or a population of cells derived from a single clone.

A membrane compartment, such as a cell, such as a mammalian cell, can include a reporter enzyme activity or include a reporter gene encoding a reporter enzyme that is operably linked to at least one expression control sequence. Preferably, the expression control sequence can modulate the expression of the reporter gene to result in a reporter enzyme activity made in response to a stimulus, such as a test chemical (see, PCT/US97/17395 to Whitney et al., filed Sep. 25, 1997).

The reporter enzyme activity is preferably beta-lactamase, beta-galactosidase, luciferase, chloramphenicol acetyltransferase, beta-glucuronidase, alkaline phosphatase, or any other reporter enzyme activity having a detectable readout that preferably is detectable within a membrane compartment. Preferably, the reporter enzyme activity is beta-lactamase, more preferably a cytosolic beta-lactamase. The reporter enzyme activity can be produced or localized within a membrane compartment, such as a cell, such as a mammalian cell.

The inhibitor of the reporter enzyme activity inhibits the enzymatic activity of the reporter enzyme activity and can be any class of inhibitor, but is preferably an irreversible inhibitor of the reporter enzyme activity. An irreversible inhibitor refers to an irreversible inhibitor as that term is known in the art and does not refer to an immediate and absolute inhibition of a reporter enzyme activity. For example, an inhibitor of a reporter enzyme activity can be a substrate for a reporter enzyme activity and be acted upon by the reporter enzyme activity. However, at some point the reporter enzyme activity is substantially irreversibly inhibited by the irreversible inhibitor by, for example, covalent crosslinking of the active site of the enzyme by the irreversible inhibitor. Preferably, the inhibitor of the reporter enzyme activity can diffuse through a membrane (is membrane permeant) so that it can inhibit the activity of a reporter enzyme activity within a membrane compartment, such as cytosolic or intracellular reporter enzyme activities, so that background reporter enzyme activity can be inhibited at least to the extent that background enzyme activity within the membrane compartment can be inhibited to be useful in the methods of the present invention. The inhibitor of a reporter enzyme activity can enter the membrane compartment by ways other than diffusion through the membrane, such as active transport, an ion exchanger, passage through openings of membrane channels or by transient permeabilization of the compartment by means such as osmotic shock, electroporation, or liposome or viral capsid delivery. In such instances, membrane compartments need not be lysed or otherwise treated to release the reporter enzyme activity so that the inhibitor can inhibit the reporter enzyme activity. Thus, the reporter enzyme activity is inhibited within a membrane compartment. Preferably, the reporter enzyme activity is cytosolic beta-lactamase and the inhibitor is clavulanic acid. Other such reporter enzyme activity—inhibitor pairs are known in the art and can be used in the present invention. The concentration of inhibitor within the membrane compartment can be such that background reporter enzyme activity within the membrane compartment is inhibited, but the de novo reporter enzyme activity made later within the membrane compartment is not substantially inhibited. Such concentrations of inhibitor of a reporter enzyme activity need not be exact, but are preferably such that most background reporter enzyme activity is inhibited and most de novo reporter enzyme activity is not inhibited.

Such a concentration and conditions useful for the methods set forth in the present invention can be determined by contacting a sample comprising at least one membrane compartments having background reporter enzyme activity with concentrations of an inhibitor of the reporter enzyme activity and determining background reporter enzyme activity in the sample to determine the concentration necessary to inhibit background reporter enzyme activity. Then, de novo reporter enzyme activity can be introduced into the sample by, for example, inducing the expression of reporter enzyme activity within a cell. The conditions that result in maximal inhibition of background reporter enzyme activity while minimally inhibiting the de novo reporter enzyme activity are preferable because such conditions result in an enhanced signal-to-noise ratio of de novo reporter enzyme activity to background reporter enzyme activity.

Preferably, after the inhibition of background reporter activity, the concentration of the inhibitor of a reporter enzyme activity within a membrane compartment can be reduced. This can be accomplished by, for example, washing membrane compartments using established methods such as aspiration, filtration or centrifugation to separate cells from a sample and resuspending or contacting the cells with wash media (such as tissue culture media) or wash solution (such as buffer, such as PBS) that has a reduced concentration of inhibitor of a reporter enzyme activity, including no inhibitor of a reporter enzyme activity, such that, for example, inhibitor of a reporter enzyme activity within the membrane compartment will transfer by mass action into the surrounding solution. The volume of wash media or wash solution used can be greater or less than the volume of solution in contact with the cells prior to washing, and is preferably between about 0.1 and about 0.5 times the volume of solution in contact with the cells prior to washing. The greater the volume of wash media or wash solution used, the faster the inhibitor of a reporter enzyme activity will be washed out of the membrane compartment. The wash media or wash solution can comprise a test chemical and the wash media or wash solution need not be removed from the cells, but can be removed by acceptable methods, at a later time. The amount of time that the cells are in contact with a wash media or wash solution sufficient to be useful in the present invention is dependent upon the cell—inhibitor of a reporter enzyme activity pair and the conditions of the method (such as temperature and ionic strength of media or solution). Wash times can be between about five seconds and greater than about three hours, preferably between about thirty seconds and about thirty minutes, and more preferably between about one minute and about ten minutes. Useful wash times, volumes of wash media or wash solution used, and wash conditions can be determined using the methods of the present invention to confirm that the time and conditions used are useful in the present invention.

Alternatively, a membrane permeant compound or a compound that is made in a membrane compartment (such as an enzyme or protein such as beta-lactamase inhibitor protein), or a compound that is injected or otherwise placed or forced into a membrane compartment, and reduces the active concentration of the inhibitor of a reporter enzyme activity within the membrane compartment can also be used. The reduction of the concentration of inhibitor within the membrane compartment reduces the inhibition of de novo reporter enzyme activity that is later provided in the membrane compartment and thus increases the signal-to-noise ratio of the de novo reporter enzyme activity to background reporter enzyme activity.

The substrate for a reporter enzyme activity can be any substrate for the reporter enzyme activity that can be detected, or in the alternative, at least one product of the reporter enzyme activity on the substrate can be detected. Such substrates are known in the art for a particular reporter enzyme activity. Preferably, the substrate or at least one product of the reporter enzyme activity is detectable by, for example, radioactivity measurement or optical methods such as absorbance, luminescence or fluorescence intensity, half-life or polarization measurements, as they are known in the art. The substrate or a precursor to a substrate is preferably membrane permeant at least to the extent that the reporter enzyme activity (preferably de novo reporter enzyme activity) can be detected within a membrane compartment. Preferably, the substrate is for beta-lactamase, such as CCF2/AM. For example, the compound CCF2/AM is membrane permeant so that beta-lactamase activity within a membrane compartment can be detected. Upon entry of CCF2/AM into a cell, endogenous esterase converts CCF2/AM into CCF2. CCF2 is more charged than CCF2/AM and thus preferentially localizes within the membrane compartment and thus becomes more membrane impermeant than CCF2/AM (see, U.S. Pat. No. 5,741,657 to Tsien et al., issued Apr. 21, 1998; and WO 96/23810 to Tsien et al., published Aug. 8, 1996). In certain cases, a membrane permeant compound that is not a substrate for a reporter enzyme activity can be transformed into a membrane impermeant enzyme substrate in the membrane compartment. Such is the case with CCF2/AM and CCF2. The structure of CCF2/AM is as follows:

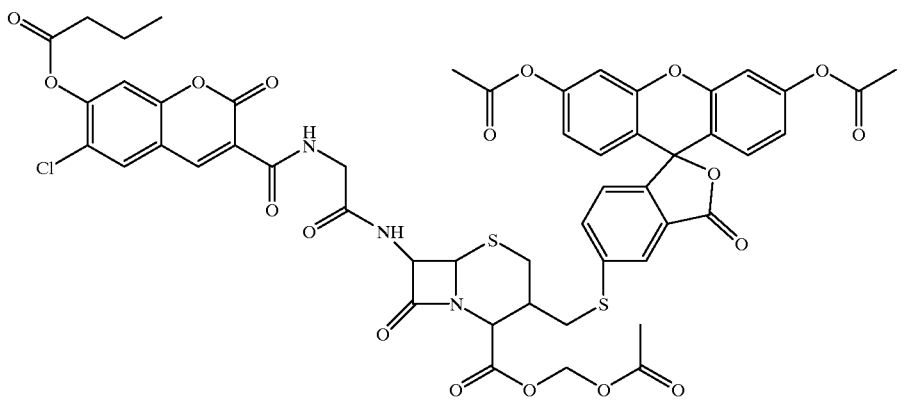

CCF2-AM

This and other methods of this invention are useful because background reporter enzyme activity is reduced by the inhibitor, which allows de novo reporter enzyme activity to be detected. Thus, with reduced background reporter enzyme activity, de novo reporter enzyme activity is preferentially detected.

The reporter enzyme activity can be detected in the sample before or after a test chemical, which can be a modulator, is contacted with the sample. The test chemical can be contacted with the sample before, contemporaneously, or after the inhibitor of a reporter enzyme activity is contacted with the sample. The substrate for a reporter enzyme activity can be contacted with the sample before, contemporaneously, or after the inhibitor of a reporter enzyme activity is contacted with the sample. Preferably, the reporter enzyme activity in the sample is detected within a membrane compartment, such as a mammalian cell. Alternatively, the reporter enzyme activity can be detected in the media suspending the membrane compartments (such as reporter enzyme secreted into the media) or in extracts of the membrane compartments (such as cell lysates).

Preferably, reporter enzyme activity is detected in membrane compartments using substrates that provide a luminescence, chromogenic or fluorescent readout of reporter enzyme activity. Reporter enzyme activity within a membrane compartment with a luminescence, chromogenic or fluorescent readout can be detected by established methods, such as photon counting, absorbance or fluorescence detection methods. Furthermore, FACS can be used to detect and optionally sort cells that have a fluorescent readout of reporter enzyme activity using methods known in the art. Preferably, in all methods of the present invention, the readout from a sample is compared to the readout from an appropriate control sample, such as a sample that does not contain the de novo reporter enzyme activity. Other appropriate controls are known and can be confirmed using well-known methods.

The methods of the present invention also include the step of optionally contacting the sample with a composition that degrades or otherwise inhibits an activity of the inhibitor or a reporter enzyme activity. The composition that inhibits the inhibitor of a reporter enzyme activity can be contacted with the sample at any time during the method, but is preferably contacted with the sample after the inhibitor is contacted with the sample and before a test sample is contacted with sample. In such a procedure, background reporter enzyme activity is reduced using the inhibitor before a test compound is contacted with the sample so that background reporter enzyme activity is reduced. The addition of the composition that inhibits the inhibitor of a reporter enzyme activity thus reduces the concentration of inhibitor of a reporter enzyme activity in the sample. Thus, when a test compound is contacted with a sample, reporter enzyme activity that is made in response to the test compound remains active due to the decreased concentration of inhibitor of a reporter enzyme activity in the sample. Accordingly, the signal-to-noise ratio of the assay increases because the background reporter enzyme activity is reduced and the concentration of the inhibitor of a reporter enzyme activity is reduced prior to the appearance of de novo reporter enzyme activity. The concentration of enzyme substrate, inhibitor, and compound that degrades the inhibitor and assay times and conditions can be determined using routine experimentation to increase the signal-to-noise ratio of such an assay.

Compounds that deactivate, degrade or otherwise inhibit the inhibitor of a reporter enzyme activity can be any compound that has the desired activity. Preferably, such compounds are membrane permeant so that the concentration of inhibitor of a reporter enzyme activity within a membrane compartment can be decreased in situ. Both membrane permeant and, non-membrane permeant compounds that deactivate, degrade or otherwise inhibit an inhibitor of a reporter enzyme activity can be used. For a beta-lactamase activity, enzymes that degrade inhibitors of beta-lactamase activity (such as clavulanic acid) are preferred. Preferred reporter enzyme activities are beta-lactamases that are not inhibited by the inhibitor of a reporter enzyme activity or convert the inhibitor of a reporter enzyme activity to an inactive form. Other such enzymes can be identified by screening enzyme pairs, one member (reporter enzyme activity) that is inhibited by the inhibitor to a first degree and another member (inactivator of the inhibitor of a reporter enzyme activity) that is inhibited by the inhibitor to a second degree, (which is less than the first degree). Likewise, preferable concentrations of reagents, times and conditions of reactions can be determined using the methods of the present invention to determine such conditions that lead to an increased signal-to-noise ratio of the assay.

In this aspect of the present invention, the membrane compartment can be separated in whole or in part from the original sample for procedures such as washing the membrane compartment using established methods such as filtration, centrifugation or removal of medium from the cells followed by resuspending or contacting the cells with a solution or media that contains a reduced (or no) concentration of inhibitor. Alternatively, such separating and washing procedures can be eliminated when a compound to degrade the inhibitor of a reporter enzyme activity is used in this method. Such a method is termed a homogeneous assay because such washing or separating steps are not required. Such homogeneous methods are particularly well suited for automation and high throughput screening procedures because robotic steps, and the hardware and software needed for such robotic steps, are reduced. Thus, such homogeneous assays become more efficient.

A further aspect of the present invention is a method for increasing the dynamic range of a reporter enzyme activity assay, comprising the steps of contacting a sample comprising a membrane compartment containing a reporter enzyme activity with an inhibitor of a reporter enzyme activity, contacting said sample with a substrate for said reporter enzyme activity, and determining the activity of said reporter enzyme activity. This aspect of the present invention utilizes the compounds, methods and procedures of the present invention to increase the useful loading time for the substrate in an enzyme assay that includes a de novo reporter enzyme activity within a membrane compartment.

In addition to increasing the signal-to-noise ratio of a reporter enzyme activity assay, the present invention also increases the dynamic range of a reporter enzyme activity assay using the same methods, procedures, and reagents of the present invention. The dynamic range of a reporter enzyme activity assay is the range of reporter enzyme activity over which the assay can be qualitative, quantitative or semi-quantitative. In the present invention, by increasing the signal-to-noise ratio of the assay, the assay can detect lower amounts of de novo reporter enzyme activity due to lower background reporter enzyme activity. Thus, the dynamic range of the assay is increased in at least being more sensitive at the lower levels. Also, the upper detection limits can be extended for the same reasons, which allows for an even further increase in the dynamic range of such an assay.

As with other aspects of the present invention, the increase in the dynamic range of an assay can be evaluated using methods of the present invention under various conditions (such as time, temperature, and buffer composition) and concentrations and types of reagents. One need only determine the dynamic range of an assay prior to the use of an inhibitor or a compound that degrades or otherwise inactivates the inhibitor. Then, the assay can be performed using a variety of reagents and conditions to confirm that the dynamic range of the assay has been increased using the methods of the present invention.

Another aspect of the present invention is a method for extending the useful loading time or assay measurement time of a reporter enzyme activity assay, comprising the steps of contacting a sample comprising a membrane compartment containing a reporter enzyme activity with an inhibitor of a reporter enzyme activity, contacting said sample with a substrate for said reporter enzyme activity, and determining the activity of the reporter enzyme activity. This aspect of the invention utilizes the compounds, methods and procedures of the present invention to increase the useful loading time of a reporter enzyme activity assay that includes a reporter enzyme activity within a membrane compartment.

In certain membrane compartment—enzyme substrate pairs, there is only a limited amount of the enzyme substrate available within the membrane compartment. If the amount of enzyme substrate available within a membrane compartment is relatively low and the amount of background reporter enzymatic activity is relatively high in the membrane compartment, then the background reporter enzymatic activity within the membrane compartment can utilize a large proportion of available enzyme substrate. Thus, the background of such an assay would be high and the signal (de novo reporter enzyme activity) could be virtually undetectable. Such enzyme assays are called "runaway assays."

Under these circumstances, de novo reporter enzyme activity may not be detectable because of the lack of enzyme substrate available. Under these circumstances, the use an inhibitor of a reporter enzyme activity, especially a membrane permeant inhibitor of a reporter enzyme activity, would be beneficial because the inhibitor would reduce the amount of background reporter enzyme activity prior to appearance of de novo reporter enzyme activity. Preferably, the assay would be performed by first adding the inhibitor of a reporter enzyme activity to the sample to inhibit background reporter enzyme activity. Then, the assay could be performed in the usual manner to obtain useful and appropriate signal-to-noise ratios.

These assays are preferably performed using mammalian cells, membrane permeant inhibitors, membrane permeant enzyme substrates, and intracellular or cytosolic reporter enzyme activities. These methods can be used to increase the signal-to-noise ratio of such assays, especially assays that result in de novo reporter enzyme activity appearing in response to a stimulus, such as a test chemical.

This aspect of the invention also utilizes the compounds, methods and procedures discussed herein to increase the assay time of an enzyme assay that includes a reporter enzyme activity within a membrane compartment. At times, runaway assays are problematic because the high background reporter enzyme activity competes with reporter enzyme activity for enzyme substrate. At high levels of background enzyme activity and low levels of enzyme substrate, a narrow window of time for which useful results can be obtained often results. By decreasing the background reporter enzyme activity using an inhibitor, the window of time for which useful results can be obtained is increased. Thus, the assay of the present invention can be used to extend the time for which such reporter enzyme activity assays are useful, and allow the determination of such valuable parameters as the kinetics of reporter enzyme activity produced in response to a stimulus, such as a test chemical. The concentration and type of reagents and assay conditions useful for these methods can be confirmed by screening compounds, reagent and condition in the assay for the desirable characteristics discussed herein.

A further aspect of the present invention is a method for profiling the level of a reporter enzyme activity, comprising the steps of contacting a sample comprising a membrane compartment with an inhibitor of a reporter enzyme activity, contacting the sample with a substrate for the reporter enzyme activity, and determining the activity of the reporter enzyme activity.

This aspect of the invention also utilizes the compounds, methods and procedures discussed herein to profile the level of a reporter enzyme activity in a membrane compartment, such as in a cell. The use of different amounts of an inhibitor of a reporter enzyme activity in a sample can be used to inhibit different levels of a reporter enzyme activity. When the level of inhibitor of a reporter enzyme activity exceeds the amount of the reporter enzyme activity in the sample, then there will be a reduced read-out for the level of reporter enzyme activity in the sample.

As the amount of reporter enzyme activity exceeds the amount of inhibitor of a reporter enzyme activity, then the readout for the level of the reporter enzyme activity in the sample will increase. The amount of reporter enzyme activity inhibited by an amount of an inhibitor of a reporter enzyme activity can be used to calibrate the assay in a qualitative, semi-quantitative, or quantitative mode. Thus, the present invention provides a threshold, semi-quantitative, or qualitative method for determining the amount of reporter enzyme activity in a sample.

This method is particularly useful for detecting or profiling the level of expression of a reporter enzyme activity in response to a stimulus, such as a test chemical. For example, several samples having at least one membrane compartment with a reporter enzyme activity can be contacted with the same test chemical at the same (or different) concentrations. These samples can be contacted with different concentrations of an inhibitor of a reporter enzyme activity before or after the sample is contacted with the test chemical. The amount of a reporter enzyme activity in the sample can then be determined using methods set forth in the present invention. By comparing the resulting readouts, the amount of reporter enzyme activity produced by the sample can be determined based on the profiles of reporter enzyme activity expression in the different samples. This method is useful, for example, for profiling the expression of a reporter enzyme activity in response to a test chemical to determine the concentration dependence of reporter enzyme activity produced in response to different concentrations of test chemical, which provides valuable pharmacokinetic information regarding test chemicals.

A further aspect of the present invention is a method for modulating the threshold reporter enzyme activity in a reporter enzyme activity assay, comprising the steps of contacting a sample comprising a membrane compartment with an inhibitor of a reporter enzyme activity, contacting the sample with a substrate for the reporter enzyme activity, and determining the reporter enzyme activity. This aspect of the invention also utilizes the compounds, methods and procedures of the present invention to modulate the threshold activity of a reporter enzyme activity assay rather than to profile the level of a reporter enzyme activity.

As discussed above, inhibitors of a reporter enzyme activity can be used to measure a threshold activity of a reporter enzyme activity based on the concentration of inhibitor of a reporter enzyme activity in a sample. In this aspect of the present invention, the inhibitor of a reporter enzyme activity is present in the sample at a concentration that can inhibit reporter enzyme activity at a determined level. Thus, a determined level of reporter enzyme activity is inhibited, so that only samples having reporter enzyme activity above the determined level of expression will exhibit a readout of reporter enzyme activity. This method is useful, for example, for determining if a cell exhibits a level of reporter enzyme activity above a threshold level in response to a test chemical, which provides valuable pharmacokinetic information regarding test chemicals.

Another aspect of the present invention is a method for identifying an inhibitor of a reporter enzyme activity, comprising the steps of contacting a sample comprising a membrane compartment containing a reporter enzyme activity with at least one test chemical, contacting the sample with a substrate for the reporter enzyme activity, and determining reporter enzyme activity (wherein the reporter enzyme activity is within the membrane compartment). This aspect of the invention also utilizes the compounds, methods and procedures of the present invention to identify a reporter inhibitor of an enzyme activity. This method uses membrane compartments that contain a reporter enzyme activity for which an inhibitor is sought. The reporter enzyme activity can be, for example, an intracellular or cytosolic reporter enzyme activity expressed within a mammalian cell. The level of reporter enzyme activity within the membrane compartment can be determined or previously established using methods known in the art prior to the addition of a test chemical to determine initial reporter enzyme activity levels. The sample can be contacted with at least one test chemical at at least one concentration for at least one period of time under at least one set of conditions (such as temperature and solution conditions). The reporter enzyme activity in the sample, such as in a membrane compartment, is then determined. Test compounds that reduce the level of reporter enzyme activity can be inhibitors of the enzyme activity. That inhibitory activity can be confirmed by in vitro testing of preparations of reporter enzyme activity isolated from the cell to determine the kinetics of the inhibitor and the reporter enzyme activity. This method is useful for identifying chemicals that are useful in the methods of the present invention.

A further aspect of the present invention is a method for detecting membrane permeability, comprising the steps of contacting a sample comprising a membrane compartment containing a reporter enzyme activity with a non-permeant inhibitor of a reporter enzyme activity, contacting the sample with a substrate for the reporter enzyme activity, and determining the reporter enzyme activity (wherein the reporter enzyme activity is within the membrane compartment.)

This aspect of the invention also utilizes the compounds, methods and procedures of the present invention to measure membrane permeability under a variety of conditions and in response to test chemicals. In this method, membrane compartments that contain a reporter enzyme activity, such as mammalian cells expressing a cytosolic reporter enzyme activity are contacted with a test chemical or subjected to a set of conditions (such as reduced or elevated temperature). The sample is also contacted with a membrane permeable inhibitor of the reporter enzyme activity. The amount of reporter enzyme activity in the sample, preferably an intracellular or cytosolic enzyme, is then detected. If the ability of the inhibitor to pass through the membrane has been altered by the test chemical or conditions, or a combination of the two, then the membrane permeability of the cell has been altered. If the reporter enzyme activity in the sample is reduced below expected levels, then the permeability of the membrane as to the inhibitor has increased. Likewise, if the reporter enzyme activity in the sample remains substantially constant or increases then the permeability of the membrane as to the inhibitor has not changed or may have decreased. This method is useful for monitoring membrane permeability in response to test chemicals or conditions to determine their pharmacokinetic effects.

Another aspect of the present invention is a method for detecting a reporter enzyme activity, comprising the steps of contacting a sample comprising a membrane compartment containing a reporter enzyme activity with an inhibitor of a first reporter enzyme activity (wherein the inhibitor of a first reporter enzyme activity does not inhibit a second reporter enzyme activity), contacting the sample with a substrate for the first reporter enzyme activity and a substrate for the second reporter enzyme activity (wherein the substrate for the first reporter enzyme activity and the substrate for the second reporter enzyme activity are the same) and determining the activity of the first reporter enzyme activity, the second reporter enzyme activity, or the first reporter enzyme activity and the second reporter enzyme activity.

This aspect of the invention also utilizes the compounds, methods and procedures of the present invention to use at least two enzyme activities that have the same substrate, but have different sensitivities to an inhibitor, in order to perform a multiple labeled reporter enzyme activity assay. For example, a membrane compartment, such as a mammalian cell, can contain at least two nucleic acid sequences that encode at least two corresponding reporter enzyme activities. These nucleic acid sequences can be linked to one or more expression control sequences that can regulate the expression of the nucleic acid sequences encoding the reporter enzyme activities, preferably in response to different stimuli. The different reporter enzyme activities preferably are of the same type, such as beta-lactamases, but have different susceptibilities to beta-lactamase inhibitors and can have different affinities for different beta-lactamase substrates. Such susceptibilities and affinities can be determined by contacting reporter enzyme activities with different inhibitors and different substrates and measuring the response of the reporter enzyme activities to these compounds.

Cells that have such constructs can be used as duel reporters for the stimulation or repression of at least one of the expression control sequences in response to a stimulus, such as a test compound or condition, such as temperature, salinity, ion concentration or the like. Reporter enzyme activity in the sample is then detected as has been described. If desired, the sample can be contacted with an inhibitor to which the two reporter enzyme activities have different sensitivities. In this aspect of the invention, the inhibitor of a reporter enzyme activity will preferentially inhibit at least one of the reporter enzyme activities, thereby allowing the preferential detection of the other reporter enzyme activity. This simple system allows for the differentiation of the two enzyme reporter activities, and can thus distinguish their modulation (such as activation or repression) by test chemicals. This aspect of the invention is useful for determining if one or more test compounds modulate the expression of more than one reporter enzyme activities, such as is performed in assays that screen compounds for cellular activity, such as therapeutic activity.

Another aspect of the present invention is a composition, comprising at least one membrane compartment comprising a reporter gene. The membrane compartment can also comprise a reporter enzyme activity. The composition can further comprise a substrate for a reporter enzyme activity, and can also comprise an inhibitor of a reporter enzyme activity. A composition of the present can also include a compound that degrades an inhibitor of a reporter enzyme activity. A composition of the present invention can have any combination of the elements, and these elements can be provided within the membrane compartment. This aspect of the invention also utilizes the compounds, methods and procedures discussed herein to provide at least one cell useful, for example in the methods of the present invention. Such compositions can be used in the methods of the present invention.

The present invention also includes kits comprising a composition of the present invention in at least one container, such that the individual elements of the composition of the present invention can be provided in the same container, separate containers, or combinations thereof in one or more containers. For example, an inhibitor of a reporter enzyme activity can be in one container and, optionally, a membrane compartment can be provided in another container (preferably frozen or lyophilized). Optionally, a nucleic acid molecule encoding a reporter enzyme activity, such as in a plasmid or vector, can also be provided. The first container can optionally be provided in a second container that can include packaging material, external indicia of the contents, and instructions for performing at least one method of the present invention. The kits of the present invention can include hardware and/or software useful in the practice of at least one method of the present invention.

EXAMPLES

Example I

Reducing Background Enzyme Activity by Preventing Enzyme Synthesis.

The following experiments show that interference with beta-lactamase synthesis alone does not reduce background beta-lactamase activity (cytosolic) in a cell-based assay.

One day before the assay, CHO cells (an adherent cell line) expressing a cytosolic beta-lactamase reporter gene (WO 96/30540 to Tsien et al., published Oct. 3, 1996)) under control of a G-protein coupled receptor (GPCR) were plated in six clear-bottom 96- well microtiter plates at 75% confluency. The cells in half of the wells were stimulated overnight with agonist to the GPCR. Thus, these cells expressed high levels of the reporter enzyme encoded by the reporter gene. The other half of the cells were maintained without agonist in media having dialyzed fetal calf serum. This population is representative of cells with only background levels of beta-lactamase expression. These unstimulated cells expressed the reporter enzyme at levels lower than in the stimulated cells. After sixteen hours, the media was removed, the stimulated cells and the unstimulated cells were washed once by replacing the culture media by aspiration with an equal volume of phosphate buffered saline and then treated with 40 $\mu$g/ml cycloheximide in RPMI medium 1640 with 0.1% bovine serum albumin (BSA). Because CHO cells are adherent, aspiration is the preferred method of removing culture media, which is then replaced with wash media or wash solution. The wash media or wash solution can then be in turn removed by aspiration and replaced with other media or reagents. The cells were incubated at 37° C. and samples of the cells were removed at one-hour time intervals for assay of beta-lactamase activity by addition of one-sixth volume CCF2/AM aqueous loading solution containing 6 $\mu$M CCF2/AM, 24% PEG-400, 6.2% DMSO, 0.6% Pluronic F 127, 7.2 mM Tartrazine, 7.2 mM Acid Red 40 to the wells at room temperature (see, WO 96/30540 to Tsien et al., published Oct. 3, 1996; and the Provisional U.S. patent application entitled "Photon Reducing Agents for Cellular Fluorescent Assays" filed August 1, 1997,). After thirty minutes of incubation, the fluorescence from the wells was determined using a microtiter plate fluorimeter with excitation at 395/20nm and emission at 460/40nm and 530/30nm. The raw fluorescence emission values were corrected for the signal from wells without cells. The corrected signal from the blue channel (460/40nm) was divided by the signal from the green channel (530/30nm). This type of analysis is referred to as ratioing. With the gain settings used for this experiment, a population of greater than 95% blue fluorescent cells (>95% cells expressing beta-lactamase) will give a ratio of greater than about 3.0 and a population of entirely green fluorescent cells (no cell expressing any beta-lactamase) will give a ratio from about 0.1 to about 0.2. FIG. 1 shows the ratio values of cell populations containing cells expressing cytosolic beta-lactamase reporter enzyme. Every data point represents the average of cell populations in four wells with the error bars representing the standard error of quadruplicate measurements.

The values at time zero indicate that cells expressing beta-lactamase are present. Ratio values stay above 0.2 both for low and high expressing cells even after 5 hours, indicating that even in the absence of de novo reporter synthesis blue fluorescence cells (beta-lactamase positive) are present in the cell population.

Example II
Reducing Background Enzyme Activity using Enzyme Inhibitors.

To determine whether inhibitors of beta-lactamase activity can be used to inhibit cytosolic beta-lactamase reporter activity in live cells expressing beta-lactamase were treated with increasing concentrations of three inhibitors of beta-lactamase activity. Two of these inhibitors reduced reporter signal significantly at 300 $\mu$M. An irreversible inhibitor of beta-lactamase activity, clavulanic acid, reduced the reduced beta-lactamase activity in these cells to levels found in cells that do not have the reporter.

Figure 2:
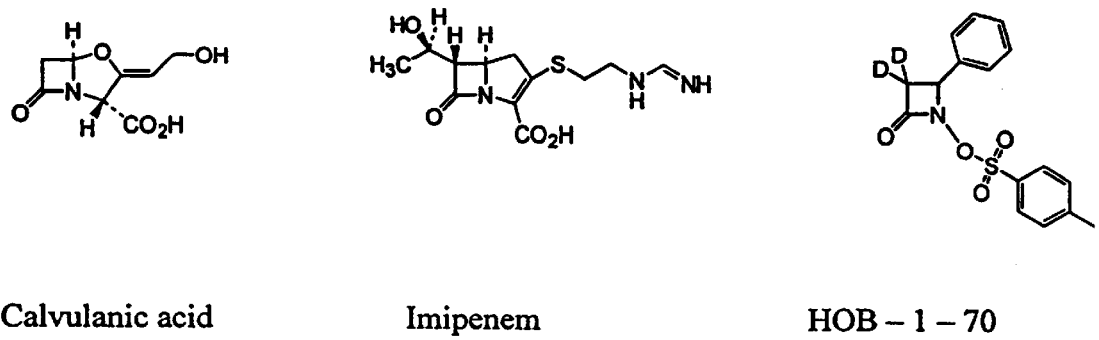
FIG. 2 represents the inhibition of cytosolic beta-lactamase reporter enzyme activity using inhibitors of beta-lactamase.
Figure 2:
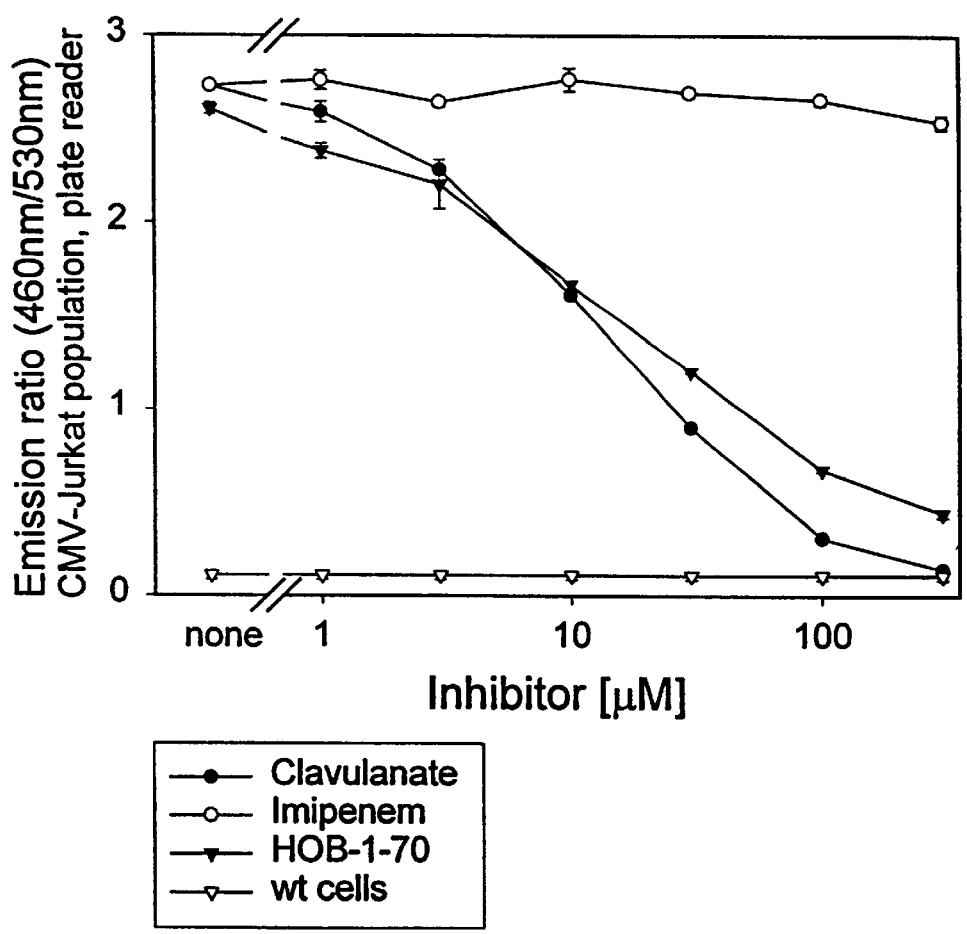

Jurkat cells (a non-adherent cell line) expressing a cytosolic beta-lactamase reporter enzyme (WO 96/30540 to Tsien et al., published Oct. 3, 1996) under the control of the constitutively active cytomegalovirus early promoter (CMV promoter) were incubated with three inhibitors: clavulanic acid, imipenem and HOB-1-70. Inhibitor concentrations ranged from 1 micro$\mu$ to 300 $\mu$M. Cells were treated for one hour at 37° C., after which beta-lactamase reporter activity was assessed as in Example I (FIG. 2).

The results obtained with wild type Jurkat cells not expressing any beta-lactamase was included as a control. Clavulanic acid at a concentration of 300 $\mu$M essentially reduced reporter beta-lactamase activity to values found for a naive Jurkat population. The inhibitor imipenem did not have a similar effect, possibly because this compound has a polar zwitterionic nature at pH 7, which may prevent its diffusion through the plasma membrane into the cell. The more hydrophobic inhibitor HOB-1-70 was not as effective as clavulanic acid in reducing beta-lactamase reporter activity. HOB-1-70 is considered to reversibly inhibit beta-lactamase activity because as 100% of the activity is recovered after 3 hours (see, Bulychev et al., JACS 117:5938–5943 (1995)). Inhibition of beta-lactamase activity by clavulanic acid is considered to be irreversible because it cross-links the active site of the enzyme in secondary reactions (see, Knowles, Acc. Chem. Res. 18:97–104 (1985)).

Example III
Removal of Enzyme Inhibitors from Cells.

To determine if excess inhibitor can be washed out of cells to allow measurement of newly synthesized cytosolic beta-lactamase reporter, cells were incubated in the presence of inhibitor, washed thoroughly and de novo synthesis of beta-lactamase measured as a function of time after the inhibitor was washed out of the cells. The results of these studies indicate that beta-lactamase synthesis and activity can be readily detected in cells that have been washed after treatment with an inhibitor of beta-lactamase.

Figure 3:
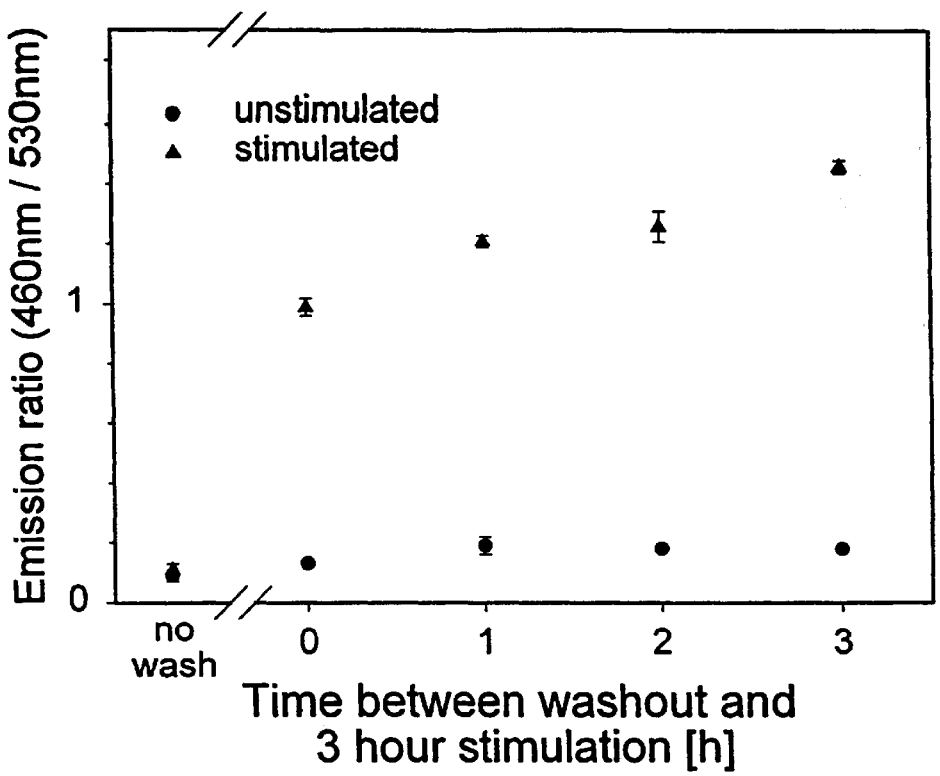
FIG. 3 represents the recovery of cytosolic beta-lactamase reporter enzyme activity after a beta-lactamase inhibitor has been washed out of cells, kept in an incubator for the indicated amount of time, followed by a 3-hour stimulation with agonist.

These studies used a Jurkat cell clone (referred to as "C2 cells" ) containing the $M_1$-receptor and a cytosolic beta-lactamase reporter gene (WO 96/30540 to Tsien et al., published Oct. 3, 1996)) regulated by a NF-AT response element. This cell line synthesizes the beta-lactamase reporter in response to $M_1$-receptor agonists. C2 cells were incubated in the presence of 100 microM clavulanic acid for sixteen hours and were either untreated or washed once with an equal volume phosphate buffered saline by centrifugation and resuspended in RPMI medium 1640 containing 10% fetal calf serum. Because C2 cells are non-adherent, washes can be accomplished by centrifuging the cell culture, removing the culture medium, and replacing the culture medium with wash solution or other reagents or media. Cells were then dispensed at a density of 100,000 cells per well in four clear-bottom 96-well microtiter plates. The cells were kept in an incubator at 37° C. fort 0, 1, 2 and 3 hours after the wash. Then the cells were either not treated or stimulated with 100 microM carbacol (an $M_1$ receptor agonist, three hours after which beta-lactamase activity in t a n was assessed as in Example I. FIG. 3 shows beta-lactamase activity for these samples. Every data point represents the average of cell populations in eight wells with the error bars representing standard error of the octuplicate measurements. In the "no-wash" control, beta-lactamase activity, both residual and synthesized de novo, was reduced because the inhibitor is present throughout the experiment that inhibited all beta-lactamase activity. Stimulation of cells, even immediately after the wash, results in de novo synthesis of beta-lactamase that can be detected. Higher beta-lactamase activity was detected in the cells as the time after the inhibitor was washed out of the cells increased.

Example IV
Inhibition of Intracellular Enzymes using Irreversible Inhibitors.

To investigate whether the inhibition of cytosolic beta-lactamase reporter enzyme by clavulanic acid is irreversible under intracellular conditions, cells containing inhibited reporter enzyme were assayed for reappearance of beta-lactamase activity with time. The results of these studies establish that intracellular beta-lactamase reporter enzyme is irreversibly inhibited by clavulanic acid under typical cell-based assay conditions.

Figure 4:
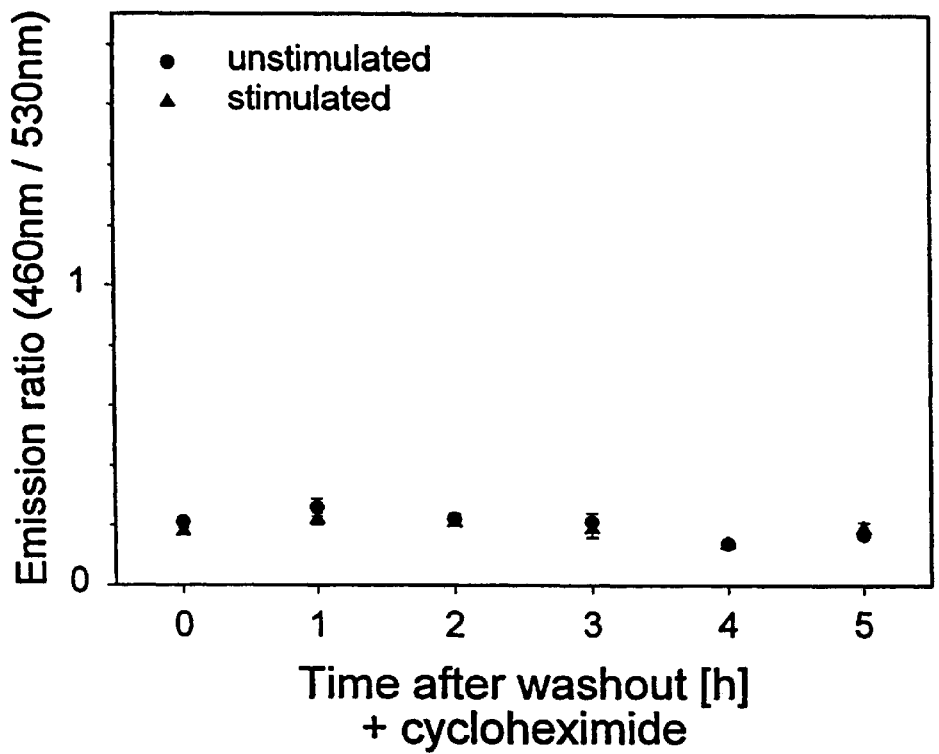
FIG. 4 represents that an inhibitor of beta-lactamase reporter enzyme activity can remain effective for extended periods of time in an intracellular environment even after the inhibitor has been removed from the medium bathing the cells.

One day before the assay, CHO cells expressing a cytosolic beta-lactamase reporter gene (WO 96/30540 to Tsien et al., published Oct. 3, 1996) under control of a G-protein coupled receptor (GPCR) were plated in six clear-bottom 96-well microtiter plates at 75% confluency in the presence of 300 $\mu$M clavulanic acid. The cells in half of the wells were stimulated overnight with an agonist to the GPCR so that these cells expressed high levels of beta-lactamase. The other half of the cells were kept without agonist in media with dialyzed fetal calf serum and expressed low levels of beta-lactamase. The unstimulated population represents cells with background levels of beta-lactamase expression. After sixteen hours the media was removed from the wells and the cells were washed once with an equal volume of phosphate buffered saline and treated with 40 $\mu$g/ml cycloheximide in RPMI medium 1640 with 0.1% bovine serum albumin (BSA). BSA was used as a substitute for serum, which may contain components that have receptor agonist activity. . The plates were incubated at 37° C. and samples of cells were removed at one-hour time intervals to determine beta-lactamase activity in the cells as in Example I. FIG. 4 shows the beta-lactamase activity in cell populations containing cells expressing beta-lactamase reporter enzyme inhibited by clavulanic acid. Every data point represents the average of cell populations in four wells with the error bars representing standard error of the quadruplicate measurements. Ratio values remained at about 0.2 both for cells expressing low and high levels of beta-lactamase even after five hours of incubation. These results indicate that the beta-lactamase present before cycloheximide treatment remains inhibited for at least five hours under typical assay conditions used for evaluating test chemicals for modulator activity. These results indicate that this method reduces background beta-lactamase reporter activity in an irreversible manner because beta-lactamase reporter activity does not reappear.

Example V
Reduction of Background Reporter Enzyme Activity ex vivo Using Irreversible Inhibitors.

This Example investigates whether background levels of preexisting cytosolic beta-lactamase activity or a high level of de novo synthesis of beta-lactamase reporter activity in unstimulated cells is the main source of background beta-lactamase activity. The prior is readily amenable to reduction by clavulanic acid pretreatment as demonstrated in Example IV. The latter source of background activity is reduced with inhibitor treatment performed at the time of substrate addition (see, Example IX). The results of this Example indicate that when the background beta-lactamase reporter activity is primarily due to preexisting enzyme, pretreatment of the cells with clavulanic acid is an effective means of lowering the background beta-lactamase reporter activity in the assay.

Figure 5:
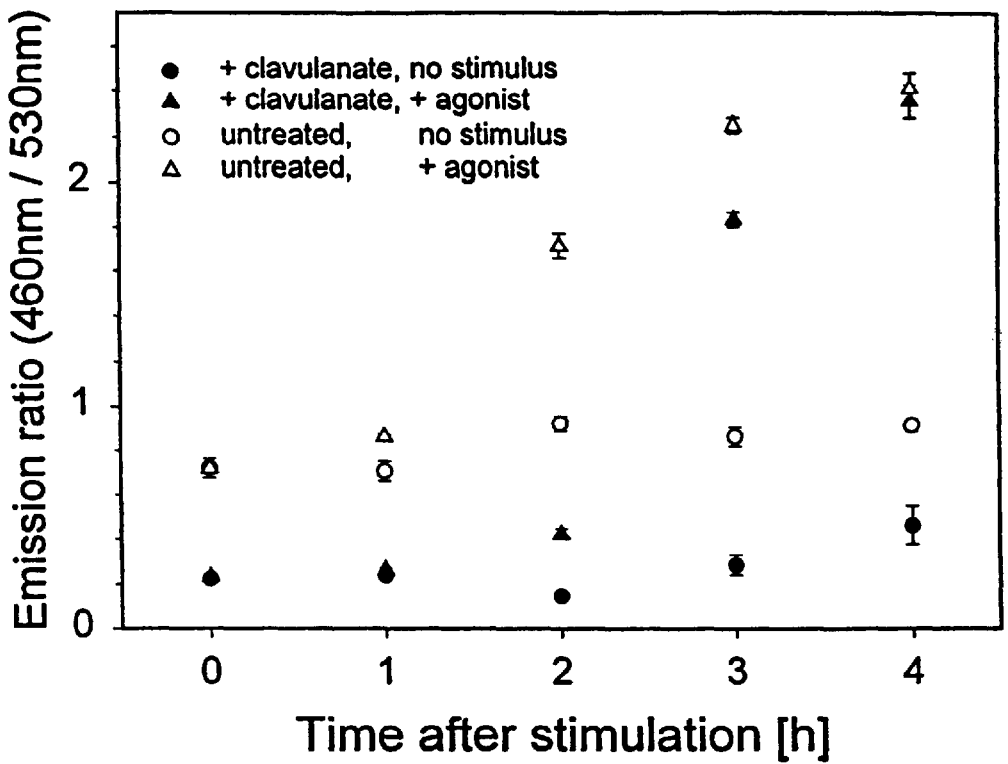
FIG. 5 represents a time course of agonist dependent induction of de novo cytosolic beta-lactamase reporter enzyme activity after a membrane permeant inhibitor of the cytosolic beta-lactamase reporter enzyme activity is removed from the cells by a wash.

One day before the assay, CHO cells expressing a cytosolic beta-lactamase reporter gene (WO 96/30540 to Tsien et al., published Oct. 3, 1996) under control of a G-protein coupled receptor (GPCR) were plated in six clear-bottom 96-well microtiter plates at 75% confluency in the presence or absence of 300 $\mu$M clavulanic acid. After sixteen hours all cells were washed once with an equal volume of clavulanic acid free medium with 0.1% bovine serum albumin. Cells in half of the wells then were stimulated with an agonist of the GPCR and the other half of the cells were kept without an agonist to the GPCR. The cells were incubated at 37° C. and samples of the cells were taken in one-hour time intervals for assay of beta-lactamase activity as in Example I. FIG. 5 shows the beta-lactamase activity in cell populations with cells that contain only de novo synthesized beta-lactamase reporter enzyme (filled symbols, clavulanic acid pretreated) and untreated controls (open symbols, no pretreatment). Every data point represents the average of cell populations in four wells with the error bars representing standard error of the quadruplicate measurements. Filled circles represent cell populations that were clavulanic acid pretreated and kept in the absence of agonist. The appearance of beta-lactamase activity in these populations after three hours is probably due to a background of de novo synthesis of beta-lactamase in unstimulated cells. In untreated and unstimulated cells (open circles) the background activity was much higher, indicating that at three hours the predominant contribution of background activity stems from enzyme already present before the assay, which was readily inhibited by clavulanic acid.

Example VI
Reduction of Background Reporter Activity in an ex vivo Agonist Assay.

To investigate whether receptor activation results in similar reporter enzyme readouts, agonist titration curves were made using cells that were either untreated or pretreated with clavulanic acid. The curve shapes of the resulting plots were very similar for untreated cells and cells pretreated with clavulanic acid. Also, untreated cells and cells treated with clavulanic acid had similar $EC_{50}$ concentrations for the agonist, but the signal-to-noise ratio was improved when cells pretreated with clavulanic acid were used in the assay.

Figure 6:
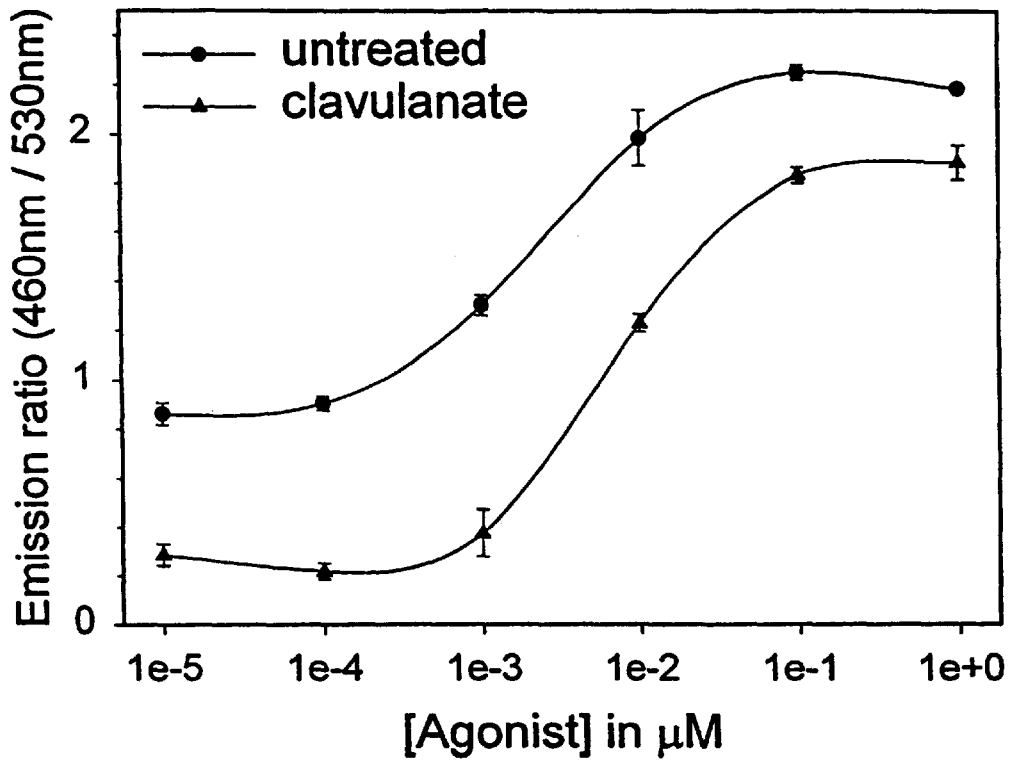
FIG. 6 represents the enhanced signal-to-background ratio obtained in a cytosolic beta-lactamase reporter enzyme activity assay that uses an inhibitor of beta-lactamase reporter enzyme activity.

One day before the assay, CHO cells expressing a cytosolic beta-lactamase reporter enzyme by a reporter gene (WO 96/30540 to Tsien et al., Oct. 3, 1996) under control of a G-protein coupled receptor (GPCR) were plated in six clear-bottom 96-well microtiter plates at 75% confluency in the presence or absence of 300 micro$\mu$ clavulanic acid. After sixteen hours all cells were washed once with an equal volume of clavulanic acid free RPMI medium 1640 with 0.1% bovine serum albumin. Cells were then exposed to increasing concentrations of agonist for the GPCR. The cells were incubated at 37° C. and beta-lactamase activity in the cells was determined after three hours as in Example I. FIG. 6 shows the increase of beta-lactamase reporter activity in the cells with agonist concentration for cells with and without clavulanic acid pretreatment. The curve shapes of the plotted ratio values were very similar, with similar $EC_{50}$ concentrations for the agonist. However, the background beta-lactamase activity was much lower in the assay using cells that were pretreated with clavulanic acid.

Example VII
Reduction of Background Enzyme Activity in vivo using a Homogeneous Assay.

The following Example describes a homogeneous assay for detecting cytosolic beta-lactamase activity in living cells using clavulanic acid. In this assay, instead of washing excess clavulanic acid from the cells before adding a test chemical, clavulanic acid in the sample is degraded by the addition of a different class or isozyme of beta-lactamase (inhibitor degrading beta-lactamase) that is not inhibited, or not inhibited to the same degree as, the beta-lactamase reporter. The clavulonic acid degrading beta-lactamase enzyme preferably is not inhibited by clavulanic acid, but does accept clavulanic acid as a substrate. In operation, the addition of the clavulonic acid degrading beta-lactamase removes clavulonic acid from the sample. Once the clavulonic acid is removed from the sample, newly synthesized beta-lactamase can be detected using methods of the present invention.

The general procedures set forth in Example VI are followed with the modification that a clavulonic acid degrading beta-lactamase is added to a sample before, with, or after a test compound. For example, one day before the assay, CHO cells expressing a cytosolic beta-lactamase reporter gene (WO 96/30540 to Tsien et al., published Oct. 3, 1996) under control of a G-protein coupled receptor (GPCR) are plated in six clear-bottom 96-well microtiter plates at 75% confluency in the presence of 300 micro$\mu$ clavulanic acid. After sixteen hours, a clavulonic acid degrading beta-lactamase is added at the same time as a test compound, such as a GPCR agonist. The samples are incubated at 37° C. and beta-lactamase activity in the sample is determined after three hours as in Example I. The predicted results of such an assay are presented in FIG. 6 (triangles) which shows an increase of intracellular beta-lactamase reporter activity similar to that obtained by washing clavulonic acid from the cells.

Example VIII
Detecting Membrane Permeable Inhibitors of Reporter Beta-lactamase.

This Example establishes that a cell expressing a cytosolic reporter beta-lactamase can be used to screen for membrane permeable inhibitors of that enzyme. A cell line expressing a reporter beta-lactamase was treated for one hour with compounds that could act as suicide or competitive inhibitors of the reporter beta-lactamase. The cells were then tested for reporter beta-lactamase activity using methods described in the present invention. Except for clavulanic acid, commercially available beta-lactam compounds or boronic acid derivatives did not substantially inhibit the reporter beta-lactamase activity at concentrations of up to 300 $\mu$M.

The general procedures described in Example VI were followed. Briefly, Jurkat cells expressing a cytosolic reporter beta-lactamase (WO 96/30540 to Tsien et al, published Oct.

Figure 7:
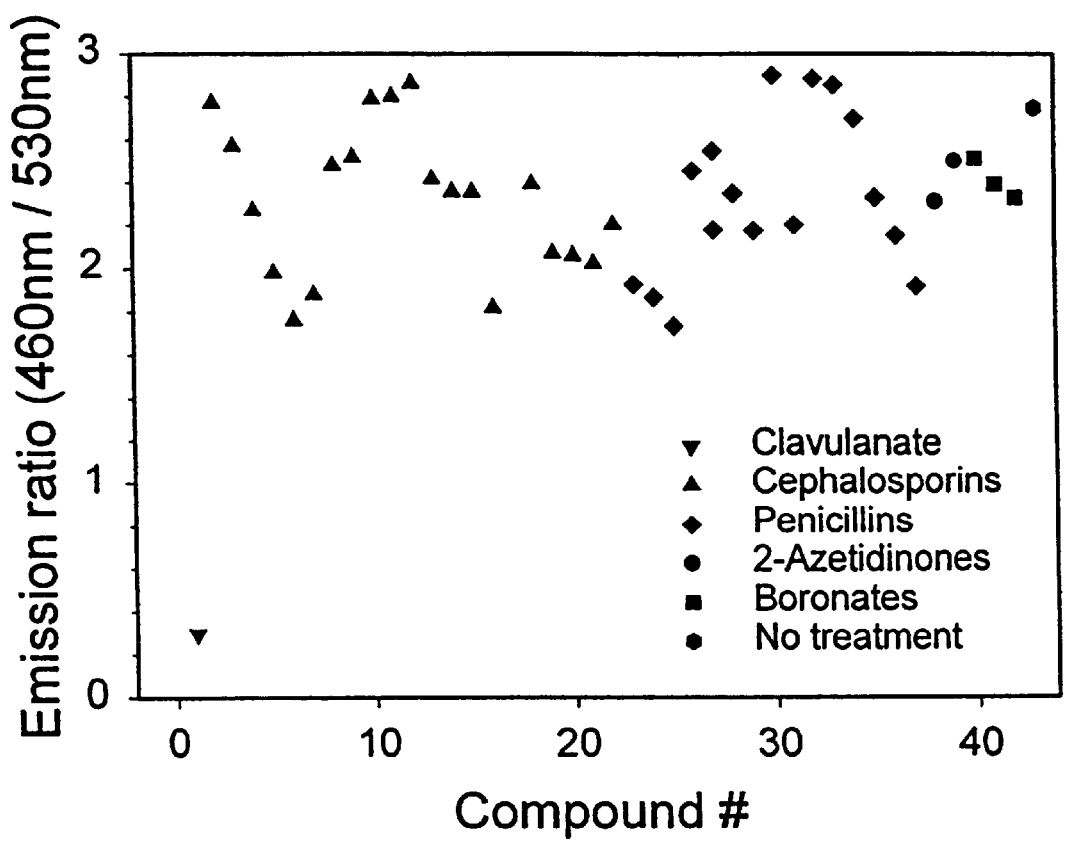
FIG. 7 represents the results of a screen to identify inhibitors of beta-lactamase reporter enzyme activity useful in the present invention.

3, 1996) were incubated with these compounds, and clavulanic acid as positive control, at concentrations from 1 μM to 300 μM. Cells were treated for one hour at 37° C., after which reporter beta-lactamase activity was assessed as in Example I. FIG. 7 shows the emission ratio data for the highest concentration of compound (300 microμ). All compounds except for clavulanic acid failed to inhibit cytosolic beta-lactamase.

The following compounds were tested for such activity in a Jurkat cell expressing cytosolic beta-lactamase under the control of the constitutively active cytomegalovirus early promoter (CMV promoter): Cefaclor, Cephalotin Sodium Salt, 7-Aminocephalosporanic Acid, Cefamandole Nafate, Cefoxitin, Cephapirin, Cefamandole, Cephaloglycin, 7-Aminodesacetoxy-Cephalosporanic Acid, Cefoperazone, Cephaloridine Hydrate, Cefadroxil, Cefmetazole, Cephalexin Hydrate, Cephalosporin C Zinc Salt Cephradine, Cefatoxim Sodium Salt, Cefazolin Sodium Salt, Ceftriazone, Cefuroxime, Phenoxymethyl-Penicillic Acid Benzyl Ester, (+)-6-Aminopenicillanic Acid, Bacampicillin, Oxacillin Sodium Salt, Piperacillian Sodium Salt, Ampicillin, Dicloxacillin, Nafcillin, Benzylpenicillin Sodium Salt, Metapicillin, Phenethicillin, Phenoxymethyl-Penicillic Acid, Amoxicillin, Moxalactam, Azlocillin, Cloxacillin Sodium Salt, 4-Acetoxy-2-azetidinone, 2-Azetidinone, 3-(Trifluoromethyl) Phenyl, Boronic acid, Sodium Borate, and Phenylboronic Acid.

Example IX
Increasing Signal-to-Noise Ratio of Reporter Beta-Lactamase Assays

To investigate whether an inhibitor of cytosolic beta-lactamase can be used to increase assay signal to noise ratio in a live cell assay, an inhibitor of the beta-lactamase was added together with CCF2 during the course of an assay. The beta-lactamase used in the cell based assays hydrolyzes about 100 molecules of clavulanic acid on average before becoming irreversibly inactivated by clavulanic acid. Consequently, cells containing less enzyme lose beta-lactamase activity in the presence of clavulonic acid as compared to cells expressing large amounts of beta-lactamase. The background beta-lactamase activity in cells treated with an inhibitor of beta-lactamase was lower than untreated cells, while activated population were less (or not) affected.

Figure 8A:
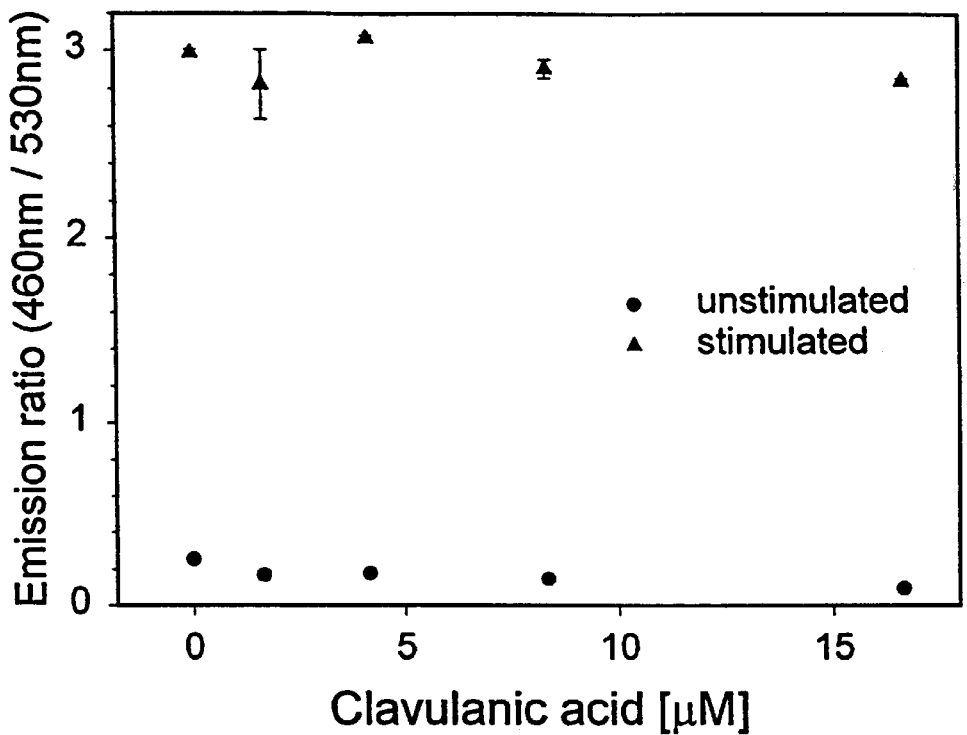
FIG. 8A represents the delivery of an irreversible inhibitor of a reporter together with a substrate for a reporter enzyme activity, which reduces background reporter enzyme activity without affecting the signal from de novo reporter enzyme activity.
Figure 8B:
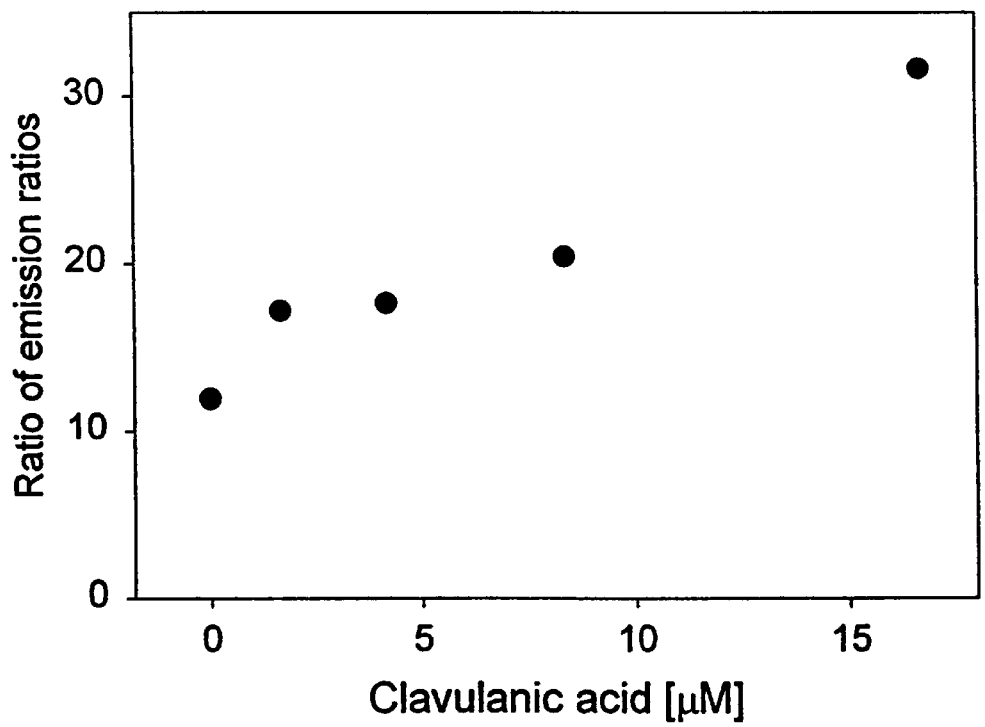
FIG. 8B represents the ratio of agonist-dependent reporter enzyme activity over background reporter enzyme activity for cells treated with increasing concentrations of an irreversible inhibitor together with a substrate for a reporter enzyme activity.

One day before the assay, CHO cells expressing a cytosolic beta-lactamase reporter gene (WO 96/30540 to Tsien et al., published Oct. 3, 1996) under control of a nuclear receptor were plated in DMEM with 10% dialyzed fetal calf serum at $2\times10^4$ cells per well in clear-bottom 96-well microtiter plates. After a few hours, an agonist against the nuclear receptor was added to the cells. The samples were incubated at 37° C. for 24 hours. Reporter beta-lactamase activity was then determined in the presence or absence of clavulanic acid. FIG. 8A shows the activity of reporter beta-lactamase in populations as compared with cells measured for beta-lactamase activity as in Example I having additional clavulanic acid present during CCF2/AM loading and fluorescent measurements. Clavulanic acid concentrations used ranged between 0 microμ and 16.7 microμ. Every data point represents the average reporter beta-lactamase activity of cell populations in three wells with the error bars representing standard error of the triplicate measurements. Circles represent reporter beta-lactamase activity in cell populations that were kept in the absence of agonist, triangle represent reporter beta-lactamase activity in cell populations activated with agonist against the nuclear receptor. Presence of clavulanic acid during loading of CCF2/AM into the cells reduced background (unstimulated) ratio levels from untreated 0.251±0.10 to a lower value of 0.090±0.015 for cells loaded in the presence of 16.7 microμ clavulanic acid, while beta-lactamase activity in stimulated cells did not change significantly. The ratio of the fluorescence from samples having stimulated cells over fluorescence from samples having unstimulated cells was improved from 11-fold for cells assayed in the absence of inhibitor to 32-fold when 16.7 microμ clavulanic acid was present (FIG. 8B). This difference represents almost a three-fold improvement in signal-to-noise ratio for this assay.

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A method for increasing the signal-to-noise ratio of a beta lactamase reporter enzyme assay, comprising:
    a) contacting a sample comprising a membrane compartment containg a gene encoding a beta lactamase reporter enzyme operably linked to an inducible promoter which exhibits background expression of beta lactamase actvity with clavulanic acid,
    b) incubating said sample with said clavulanic acid so as to inhibit said background beta lactamase activity,
    c) incubating said membrane compartment in media without said clavulanic acid, or contacting said sample with a class C beta-lactamase activity to degrade said clavulanic acid,
    d) inducing expression of a beta lactamase reporter enzyme activity
    e) contacting said sample with a substrate for said beta lactamase reporter enzyme activity, and
    f) determining the activity of said beta lactamase reporter enzyme activity,
        wherein the signal-to-noise ratio of said beta lactamase assay is increased.

2. The method of claim 1,
    wherein said membrane compartment is a cell.

3. The method of claim 1, wherein the dynamic range of said beta lactamase reporter enzyme assay is increased.

4. The method of claim 1, wherein the useful loading time or assay measurement time of said beta lactamase reporter enzyme assay is extended.

5. A method for increasing the signal-to-noise ratio of a β-lactamase assay, comprising:
    a) contacting a sample comprising a membrane compartment containg a gene encoding a beta lactamase reporter enzyme operably linked to an inducible promoter which exhibits background expression of beta lactamase actvity with clavulanic acid,
    b) incubating said sample with said clavulanic acid so as to inhibit said background beta lactamase activity,
    c) contacting said sample with a class C beta-lactamase activity that degrades said clavulanic acid, and
    d) inducing expression of a beta lactamase reporter enzyme activity,
    e) contacting said sample with a substrate for said beta-lactamase reporter enzyme activity,
    f) determining the activity of said beta-lactamase reporter enzyme activity, wherein said beta-lactamase assay is homogeneous, further wherein the signal-to-noise ratio of said beta-lactamase assay is increased.

6. A method for screening test compounds for activity as an inducer of a beta lactamase reporter enzyme activity, comprising:
   a) contacting a sample comprising a membrane compartment containg a gene encoding a beta lactamase reporter enzyme operably linked to an inducible promoter which exhibits background expression of beta lactamase actvity with clavulanic acid,
   b) incubating said sample with said clavulanic acid so as to inhibit said background beta lactamase activity,
   c) incubating said membrane compartment in media without said clavulanic acid, or contacting said sample with a class C beta-lactamase activity to degrade said clavulanic acid,
   d) contacting said sample with at least one test chemical,
   e) contacting said sample with a substrate for said beta lactamase reporter enzyme activity, and
   f) determining the activity of said beta lactamase reporter enzyme activity,
   g) optionally comparing the activity of said beta lactamase reporter enzyme activity in the presence and absence of said test chemical.

7. The method of claim 6, wherein said membrane compartment is a cell.

8. The method of claim 1, wherein said substrate is CCF2/AM.

9. The method of claim 8, wherein said determining step comprises determining the activity of said beta lactamase reporter enzyme in said membrane compartment.

10. The method of claim 1, wherein said determining further comprises making a cellular extract to lyse said membrane compartment.

11. The method of claim 5, wherein said substrate is CCF2/AM.

12. The method of claim 5, wherein said determining further comprises making a cellular extract to lyse said membrane compartment.

13. The method of claim 6, wherein said substrate is CCF2/AM.

14. The method of claim 6, wherein said determining further comprises making a cellular extract to lyse said membrane compartment.

* * * * *